(12) United States Patent
Sakaguchi et al.

(10) Patent No.: US 7,371,219 B2
(45) Date of Patent: May 13, 2008

(54) ULTRASOUND DIAGNOSIS APPARATUS OPERABLE IN DOPPLER MODE

(75) Inventors: Fumiyasu Sakaguchi, Otawara (JP); Kazuhito Nakata, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 531 days.

(21) Appl. No.: 10/839,128

(22) Filed: May 6, 2004

(65) Prior Publication Data

US 2005/0004462 A1    Jan. 6, 2005

(51) Int. Cl.
*A61B 8/06* (2006.01)
(52) U.S. Cl. ..................................... 600/455
(58) Field of Classification Search ................ 600/443, 600/447, 453–457; 128/916
See application file for complete search history.

(56) References Cited

U.S. PATENT DOCUMENTS

| | | | |
|---|---|---|---|
| RE35,371 E | | 11/1996 | Seo |
| 5,908,391 A | * | 6/1999 | Muzilla et al. ............. 600/454 |
| 5,980,458 A | * | 11/1999 | Clark ......................... 600/437 |
| 6,379,306 B1 | * | 4/2002 | Washburn et al. ........... 600/454 |
| 6,701,341 B1 | * | 3/2004 | Wu et al. .................... 709/200 |
| 2004/0102702 A1 | * | 5/2004 | Shimazaki .................. 600/437 |

FOREIGN PATENT DOCUMENTS

JP    2001-37757    2/2001

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

An ultrasound diagnosis apparatus includes a probe, a controller, a processor, and an output unit. The probe is configured to perform an interleaving scan in Doppler groups of ultrasound beam directions so as to acquire first and second Doppler-mode image frames. The controller is coupled to the probe and configured to control the first probe to treat a last group of the ultrasound beam directions for the first Doppler-mode image frame and an initial group of the ultrasound beam directions for the second Doppler-mode image frame as one Doppler group of the ultrasound beam directions. The processor is coupled to the probe and configured to detect a Doppler-mode signal based on the interleaving scan so as to prepare the first and second Doppler-mode image frames. The output unit is coupled to the processor and configured to output the prepared first and second Doppler-mode image frames.

44 Claims, 12 Drawing Sheets

ULTRASOUND DIAGNOSIS APPARATUS OPERABLE IN DOPPLER MODE

CROSS-REFERENCE TO RELATED APPLICATION

This application is based upon and claims the benefit of priority from prior Japanese Patent Application No. P2003-130330, filed on May 8, 2003, the entire content of which is incorporated herein by reference.

BACKGROUND OF THE INVENTION

1. Field of the Invention

The present invention relates to an ultrasound diagnosis apparatus which acquires Doppler-mode image frames in a Doppler-mode. The present invention also relates to a method of ultrasound scanning in a Doppler-mode.

2. Discussion of the Background

In a typical ultrasound diagnosis apparatus, transducers built in an ultrasound probe generate ultrasound pulses towards a patient body. The transducers also receive echo signals returning from the patient body as a result of the ultrasound pulse generation. The echo signals occur due to a difference of acoustic impedances among tissues of the patient body. The received echo signals are displayed as ultrasound images on a display monitor. Since the ultrasound diagnosis apparatus requires only simple and easy operations such as contacting the ultrasound probe with a surface of the patient body for acquiring the ultrasound images (e.g., a real-time two-dimensional ultrasound images), the ultrasound diagnosis apparatus is widely used for functional and/or morphological diagnoses of various organs of the patient.

An ultrasound pulse echo technique and an ultrasound Doppler technique have been developed as major techniques in the field of ultrasound diagnoses. These two techniques contribute significantly to a progress in obtaining patient body information based on echo signals returned from various organs or blood cells of the patient. Recently, B-mode images acquired by the ultrasound pulse echo technique and color Doppler images (or Doppler-mode images) acquired by the ultrasound Doppler technique are usually used in ultrasound image diagnoses.

In a color Doppler technique as an example of the ultrasound Doppler technique, a predetermined cross section inside the patient body is scanned by ultrasound pulses. When the ultrasound pulses are insonified to moving reflectors such as, for example, blood (blood cells), Doppler-mode images are acquired in accordance with Doppler frequency shifts caused in correspondence with speeds of the reflectors (e.g., blood flow velocities). In the past, the color Doppler technique was used to image blood conditions in a heart chamber where blood flows fast. Recently, however, it is also possible to apply the color Doppler technique to image a very slow blood flow such as, for example, a tissue blood flow in an abdominal organ.

When a speed of the moving reflector is measured based on the Doppler frequency shifts of the moving reflector, an ultrasound transmission and reception is repeated n (n>1) times on the moving reflector at a rate interval Tr. The speed of the moving reflector is measured based on a series of n echo signals resulting from the repetition of the ultrasound transmission and reception. In this measurement, a measurable minimum velocity Vmin of the low-speed moving reflector depends on a frequency resolution $\Delta fd$ in a frequency analysis conducted on the series of n echo signals.

The frequency resolution $\Delta fd$ may be defined by the following formula (1) when a repetition frequency of the ultrasound transmission and reception (hereinafter referred to as a rate frequency) is expressed by fr (fr=1/Tr).

$$\Delta fd = fr/n \quad (1)$$

As may be understood by the formula (1), to improve the measurable minimum velocity Vmin, it is necessary to lower the rate frequency fr. Alternatively, it may be necessary to increase the repletion number of times n of the ultrasound transmission and reception in a predetermined direction. In addition, a real time performance required for ultrasound images may be determined by the number of image frames to be displayed in a unit time (hereinafter referred to as a frame frequency) Fn. The frame frequency Fn is expressed by the following formula (2).

$$Fn = fr/n/m = \Delta fd/m \quad (2)$$

The m is the total number of scan lines which are necessary to construct one image frame. Since the frame frequency Fn and the measurable minimum velocity Vmin contradict each other, it was difficult to keep both of them in predetermined conditions at the same time. Some improvement of scan techniques, however, is provided to reduce the problem mentioned above. Such improved scan technique is disclosed, for example, in Japanese Patent Application Publication No. PS64-43237 and hereinafter referred to as an interleaving scan technique.

FIG. 1A is an illustration showing one of the interleaving scan techniques. FIG. 1B is an illustration showing another one of the interleaving scan techniques. In both FIGS. 1A and 1B, a plurality of transmission and reception directions corresponding to the scan lines (or ultrasound beam directions) (hereinafter referred to as raster directions) R1 to Rm in a sector scan are shown in upper stands. One ultrasound beam may be generated in one raster direction. The order of the ultrasound transmission and reception with respect to raster directions is shown in lower stands.

In the technique shown in FIG. 1A, the ultrasound transmission and reception is conducted in a raster direction R1 at time t1. The ultrasound transmission and reception is then conducted in a raster direction R2 at time t2. Also, the ultrasound transmission and reception is conducted in a raster direction R3 at time t3. Similarly, a set of the ultrasound transmission and reception in the raster directions R1 to R3 is conducted at times t4 to t6 and times t7 to t9. Therefore, as described above, the ultrasound transmission and reception is repeated n times (here, e.g., n=3) in each raster direction. That is, for example, the ultrasound transmission and reception is conducted in the raster direction R1 at times t1, t4, and t7. The ultrasound transmission and reception are repeated n times in every group of a predetermined number Q (here, e g., Q=3) of raster directions. The ultrasound transmission and reception is conducted at an interval Tr.

In the technique shown in FIG. 1B, the ultrasound transmission and reception is conducted in a raster direction R1 at time t1. The ultrasound transmission and reception is, however, not conducted in any raster direction at times t2 and t3. The ultrasound transmission and reception restart in the raster direction R1 at time t4. At time t5, the ultrasound transmission and reception is conducted in a raster direction R2. At time t6, the ultrasound transmission and reception is not conducted. The ultrasound transmission and reception are then conducted in raster directions R1 to R3 at times t7 to t9, respectively. Further, the ultrasound transmission and reception are conducted in raster directions R1 to R4 at times t10 to t13, respectively. Next, the ultrasound transmission and reception are conducted in raster directions R2 to R5 at times t14 to t17, respectively. After this, the ultrasound transmission and reception are repeated in a manner similar to the above description until a raster direction Rm. That is, the ultrasound transmission and reception are conducted n (here, e.g., n=4) times at an interval Ts (here, e.g., Ts=3Tr) in one raster direction. The raster direction is shifted one by one.

According to the techniques shown in FIGS. 1A and 1B, the frequency resolution $\Delta fd$ which determines the measurable minimum velocity Vmin is expressed by the following formula (3).

$$\Delta fd = fs/n = fr/Qn \qquad (3)$$

The fs (fs=1/Ts) is a repetition frequency of the ultrasound transmission and reception in each raster direction. This repetition frequency fs is one third of the rate frequency fr. The frame frequency Fn is constant. Therefore, it is possible to triplicate the measurable minimum velocity Vmin without lowering the frame frequency Fn.

However, since one Doppler-mode image frame is prepared based on the ultrasound transmission and reception in the raster directions R1 to Rm according to the technique shown in FIG. 1A, the prepared Doppler-mode image frame includes discontinuous boundaries between groups of the Q raster directions (e.g., a group of the raster directions R1 to R3 and a group of the raster directions R4 to R6) (i.e., a boundary between the raster directions R3 and R4). This is because of a time phase difference between, for example, image data prepared based on the ultrasound transmission and reception in the raster directions R1 to R3 and image data prepared based on the ultrasound transmission and reception in the raster directions R4 to R6. Therefore, the more the number of n and/or Q increases, the more noticeable the boundary discontinuity becomes in the prepared Doppler-mode image frame. Also, as the number of the groups of the raster directions increases, the boundary discontinuity appears more frequently in the prepared Doppler-mode image frame. The boundary discontinuity may particularly be likely to occur and become noticeable, for example, when a pulsant blood flow is imaged, when tissues around blood vessels are subject to a respiratory movement and/or are affected by a heart beat, and when the ultrasound probe is moved by an operator. Such boundary discontinuity disturbs ultrasound image diagnoses.

According to the technique shown in FIG. 1B, scan controls become complicated. In addition, when a color Doppler image which has a shallow perspective depth is displayed together with a B-mode image which has a deep perspective depth, a display rate frequency is required to be unified to be a rate frequency for the deep perspective depth image. Therefore, this technique has a problem of a severely lowered frame frequency Fn.

SUMMARY OF THE INVENTION

According to the first aspect of the present invention, there is provided an ultrasound diagnosis apparatus. The apparatus includes a probe, a controller, a processor, and an output unit. The probe is configured to perform an interleaving scan in Doppler groups of ultrasound beam directions so as to acquire first and second Doppler-mode image frames. The controller is coupled to the probe and configured to control the first probe to treat a last group of the ultrasound beam directions for the first Doppler-mode image frame and an initial group of the ultrasound beam directions for the second Doppler-mode image frame as one Doppler group of the ultrasound beam directions. The processor is coupled to the probe and configured to detect a Doppler-mode signal based on the interleaving scan so as to prepare the first and second Doppler-mode image frames. The output unit is coupled to the processor and configured to output the prepared first and second Doppler-mode image frames.

According to the second aspect of the present invention, there is provided an ultrasound diagnosis apparatus for obtaining first and second Doppler-mode image frames. The apparatus includes a probe, a controller, a processor, and an output unit. The probe is configured to perform an interleaving scan for each of the first and second Doppler-mode image frames. Each of the first and second Doppler-mode image frames is divided into a plurality of interleaving scan groups. The controller is configured to control the probe so that a last group of the interleaving scan groups in the first Doppler-mode image frame has a smaller size than another one of the interleaving scan groups in the first Doppler-mode image frame. The initial group of the interleaving scan groups in the second Doppler-mode image frame has a smaller size than another one of the interleaving scan groups in the second Doppler-mode image frame. The combined size of the last and initial interleaving scan groups is similar to a size of the another one of the interleaving scan groups in one of the first and second Doppler-mode image frames. The processor is coupled to the probe and configured to detect a Doppler-mode signal based on the interleaving scan so as to prepare the first and second Doppler-mode image frames. The output unit is coupled to the processor and configured to output the prepared first and second Doppler-mode image frames.

According to the third aspect of the present invention, there is provided an ultrasound diagnosis apparatus. The apparatus includes a probe, a controller, a processor, and an output unit. The probe is configured to perform an interleaving scan in Doppler groups of ultrasound beam directions so as to acquire first and second Doppler-mode image frames. The controller is coupled to the probe and configured to control the probe to perform the interleaving scan for an initial group of the second Doppler-mode image frame after the interleaving scan for a last group of the first Doppler-mode image frame. The initial group includes fewer ultrasound beam directions than a next group of the ultrasound beam directions for the second Doppler-mode image frame. The processor is coupled to the probe and configured to detect a Doppler-mode signal based on the interleaving scan so as to prepare the first and second Doppler-mode image frames. The output unit is coupled to the processor and configured to output the prepared first and second Doppler-mode image frames.

According to the fourth aspect of the present invention, there is provided an ultrasound diagnosis apparatus. The apparatus includes a probe, a controller, a processor, an output unit. The probe is configured to perform an interleaving scan in groups of ultrasound beam directions so as to acquire first and second Doppler-mode image frames. The controller is coupled to the probe and configured to control the probe to perform the interleaving scan for a last group of the ultrasound beam directions for the first Doppler-mode image frame before the interleaving scan for an initial group of the ultrasound beam directions for the second Doppler-mode image frame. The last group includes fewer ultrasound beam directions than a previous group of the ultrasound beam directions for the first Doppler-mode image frame. The processor is coupled to the probe and configured to detect a Doppler-mode signal based on the interleaving scan so as to prepare the first and second Doppler-mode image frames. The output unit is coupled to the processor and configured to output the prepared first and second Doppler-mode image frames.

According to the fifth aspect of the present invention, there is provided an ultrasound diagnosis apparatus for obtaining first and second Doppler-mode image frames. The apparatus includes an ultrasound generator, a controller, a processor, and an output unit. The ultrasound generator is configured to generate a plurality of ultrasound beams in different directions for each of the first and second Doppler-mode image frames. The controller is coupled to the ultrasound generator and configured to divide the plurality of ultrasound beams into groups. Each of a second group to one before a last group of the groups includes a first predetermined number N ($N \geq 2$) of the ultrasound beams. The last group for the first Doppler-mode image frame includes a second predetermined number M ($1 \leq M \leq N-1$) of the ultrasound beams. An initial group of the groups for the second Doppler-mode image frame includes a third predetermined number N−M of the ultrasound beams. The controller is further configured to control the ultrasound generator to repeat the N ultrasound beams more than once in every one of the second group to the one before the last group and in the last and initial groups as one group. The processor is coupled to the ultrasound generator and configured to detect a Doppler-mode signal based on echo signals resulting from the ultrasound beams and to prepare the first and second Doppler-mode image frames based on the detected Doppler-mode signal. The output unit is coupled to the processor and configured to output the prepared first and second Doppler-mode image frames.

According to the sixth aspect of the present invention, there is provided a method of ultrasound scanning. The method begins by interleaving scanning in groups of ultrasound beam directions so as to acquire first and second Doppler-mode image frames. The method continues by controlling the interleaving scan to treat a last group of the ultrasound beam directions for the first Doppler-mode image frame and an initial group of the ultrasound beam directions for the second Doppler-mode image frame as one group of the ultrasound beam directions. The method further continues by detecting a Doppler-mode signal based on the interleaving scanning, preparing the first and second Doppler-mode image frames based on the detected Doppler-mode signal, and outputting the prepared first and second Doppler-mode image frames.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the ultrasound diagnosis apparatus will be described with reference to the accompanying drawings.

In the embodiments, techniques of causing positions of one or more boundaries appearing in each of a plurality of Doppler-mode image frames to be different from among two or more of the Doppler-mode image frames are disclosed. The plurality of Doppler-mode image frames may be displayed continuously. Each of the plurality of Doppler-mode image frames is prepared based on ultrasound transmission and reception in m raster directions R1 to Rm. Them raster directions may be determined in accordance with a size of an object to be examined. Therefore, the number of raster directions to be used for one Doppler-mode image frame may be more than or less than m. The raster directions R1 to Rm are divided by the predetermined number Q so that a group of Q raster directions or more groups are prepared. The first and second embodiments will be described in the specification for an exemplary purpose only, and the ultrasound diagnosis apparatus is not limited by the embodiments. When the m is divided by the Q and the remainder is present, the first embodiment may be advantageous. When the remainder is zero, the second embodiment may be advantageous. Values of the m and Q may be intentionally determined so as to apply the first or second embodiment according to the operator's preference.

First Embodiment

Figure 1A:
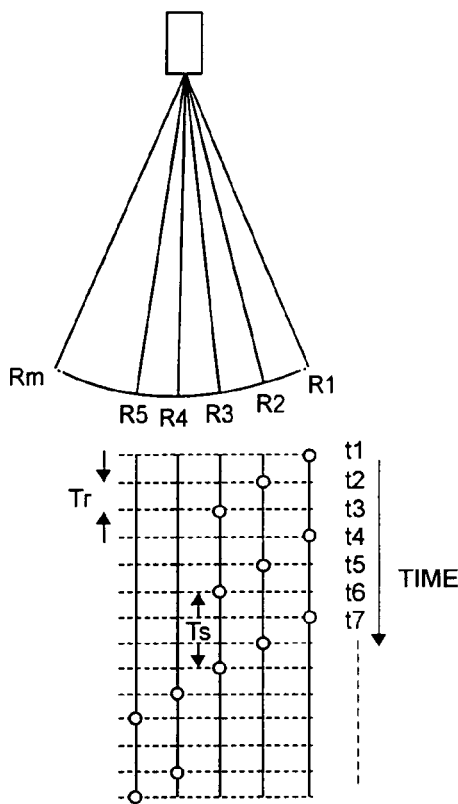
FIGS. 1A and 1B are illustrations showing examples of known interleaving scan techniques.
Figure 1B:
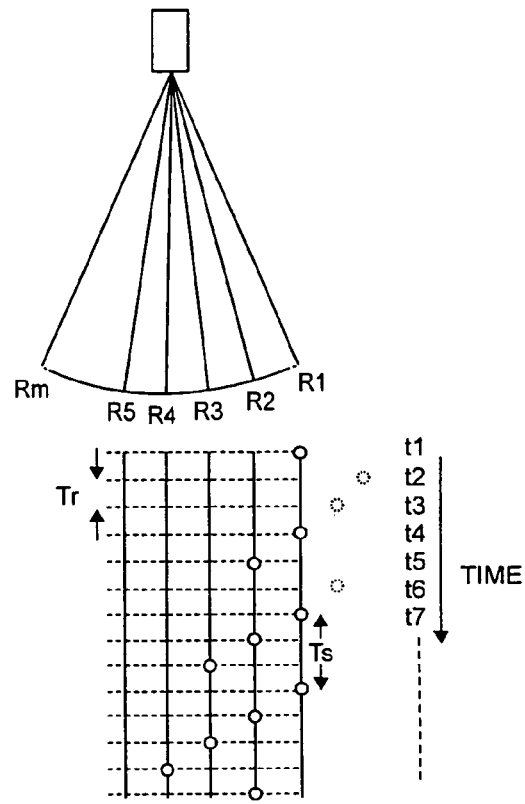
Figure 2:
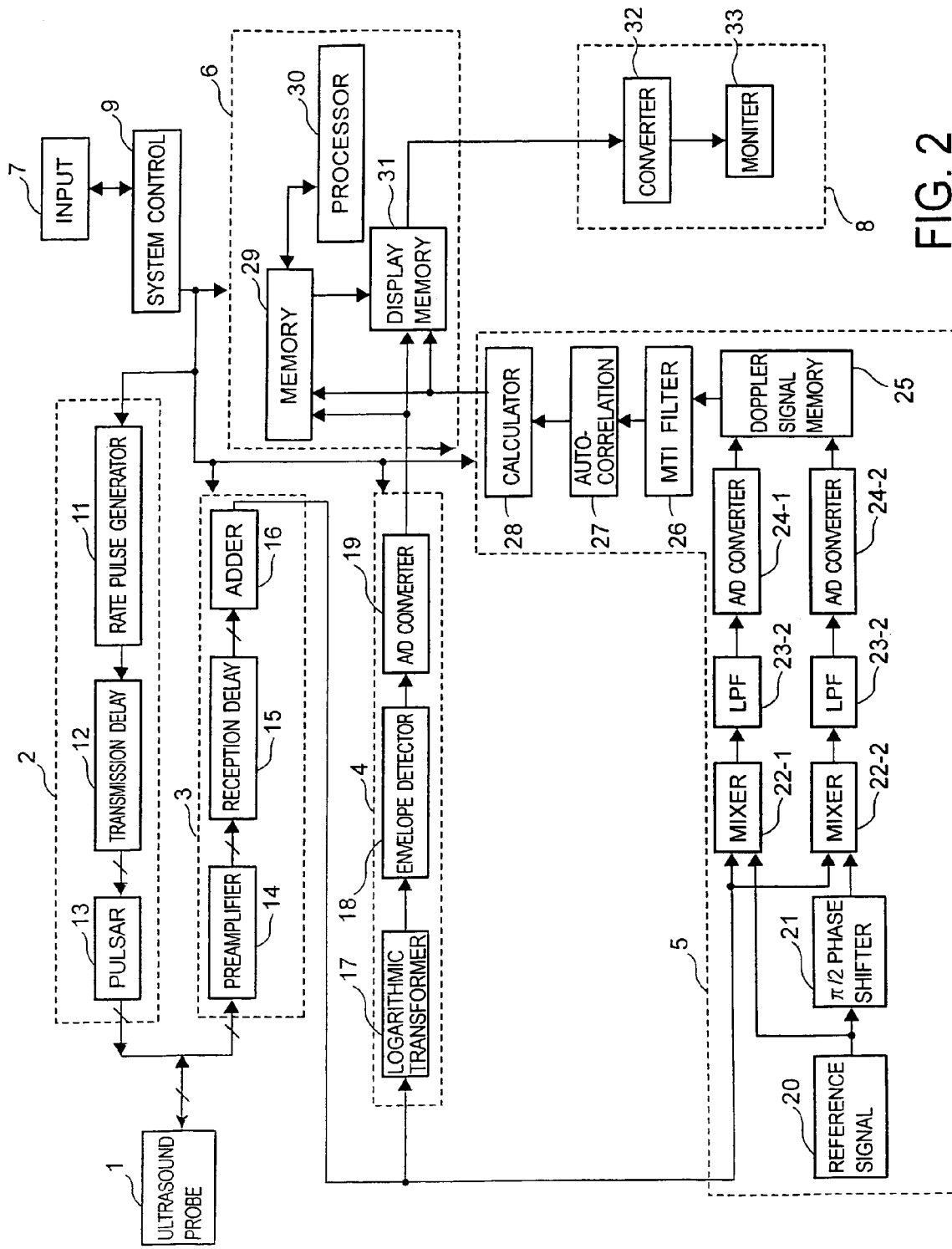
FIG. 2 is a block diagram showing an exemplary configuration of an ultrasound diagnosis apparatus according to the first embodiment of the present invention.

FIG. 2 is a block diagram showing an exemplary configuration of an ultrasound diagnosis apparatus according to the first embodiment. The ultrasound diagnosis apparatus may include an ultrasound probe 1, an ultrasound transmission unit 2, an ultrasound reception unit 3, a B-mode processing unit 4, a Doppler-mode processing unit 5, an image processing unit 6, an input unit 7, a display unit 8, and a system control unit 9.

The ultrasound probe 1 may transmit (or insonify) ultrasound pulses and receive echo signals from a patient, resulting from the transmitted ultrasound pulses while the ultrasound probe is contacting a body surface of the patient. The ultrasound probe 1 typically includes a top end having a plurality of ultrasound transducers arrayed, for example, in one-dimension. The transducers may be electro-acoustic transducer elements. The transducers convert electronic pulses into ultrasound pulses in transmission. Further, the transducers convert ultrasound pulses into electronic pulses in reception. An ultrasound frequency of the ultrasound pulses significantly affects a resolution and a sensitivity of ultrasound images. The ultrasound frequency is often determined by a thickness of the transducers. The ultrasound probe 1 is usually configured to be compact and lightweight, and is connected to the ultrasound transmission unit 2 and the ultrasound reception unit 3 through a cable. A type of the ultrasound probe 1 may be selected according to an object to be examined from various types of ultrasound probes such as, for example, a sector scan, a linear-sector scan, and a convex scan. In the following description, the ultrasound probe 1 will be described about an example of a use with a type of the sector scan. However, any type of ultrasound probe including the above-mentioned types may be applied to the ultrasound probe 1.

The ultrasound transmission unit 2 may provide the ultrasound probe 1 with driving signals so as to insonify (generate) ultrasound pulses towards predetermined directions of the patient body. In one embodiment, the ultrasound transmission unit 2 may include a rate pulse generator 11, a transmission delay circuit 12, and a pulsar 13. The rate pulse generator 11 provides the transmission delay circuit 12 with rate pulses, which determine repetition cycles of the ultrasound pulses insonified to the patient body. The transmission delay circuit 12 may include a plurality of independent delay circuits. The number of the independent delay circuits to be used may be determined to be the same as that of the transducers to be used in transmission. The transmission delay circuit 12 gives the rate pulses a delay time for making the ultrasound pulses converge to a predetermined depth. This is for obtaining a narrow width of the ultrasound beam in transmission. The transmission delay circuit 12 further gives the rate pulses another delay time for sequentially deflecting the ultrasound pulses in predetermined directions and scanning the patient body. The delayed rate pulses are supplied to the pulsar 13. The pulsar 13 may include a plurality of independent driving circuits. The number of the independent driving circuits to be used may be determined to be the same as that of the transducers to be used in the transmission as similar to the transmission delay circuit 12. The pulsar 13 drives the transducers and produces driving pulses for insonification.

The ultrasound reception unit 3 may receive echo signals from tissues of the patient body corresponding to the predetermined directions of the insonification. The echo signals result from the ultrasound pulses insonified to the patient body. The ultrasound reception unit 3 may include a preamplifier 14, a reception delay circuit 15, and an adder 16. The preamplifier 14 amplifies received signals converted by the transducers and obtains the electronic pulses, which have a preferable 'signal to noise' (S/N) rate. The reception delay circuit 15 gives output signals of the preamplifier 14 a delay time for converging the echo signals from a predetermined depth so as to obtain a narrow width of an ultrasound beam in reception. The reception delay circuit 15 further gives the output signals another delay time for sequentially changing reception directional characteristics to the received signals and for scanning the patient body. The reception delay circuit 15 supplies the adder 16 with the output signals given both the above delay time and the above another delay time.

The adder 16 adds a plurality of the output signals of the reception delay circuit 15 and, accordingly, the plurality of the output signals are output as one ultrasound data signal.

In the embodiment shown in FIG. 2, the B-mode processing unit 4 may detect B-mode signals based on the one ultrasound data signal. The B-mode processing unit 4 may include a logarithmic transformer 17, an envelope detector 18, and an analog-to digital converter (hereinafter referred to as an A/D converter) 19. The logarithmic transformer 17 performs a logarithmic transformation on an amplitude of the one ultrasound data signal so as to emphasize weak elements of the one ultrasound data signal in comparison. Typically, signals received from the insonified patient have an amplitude with a wide dynamic range of, for example, more than 80 decibels. Therefore, in order to display the signals received from the insonified patient in a regular TV monitor with a narrow dynamic range (e.g., 20 to 30 decibels), it may be necessary to perform an amplitude compression on the signals so as to emphasize the weak elements of the signals. The envelope detector 18 detects envelopes of the one ultrasound data signal on which the logarithmic transformation has already been performed. The envelope detector 18 further removes ultrasound frequency components of the envelope-detected signal and detects B-mode signals including only amplitude information of the signal, from which the ultrasound frequency components have been removed. The A/D converter 19 converts the B-mode signals output from the envelope detector 18 into digital signals.

In the embodiment illustrated in FIG. 2, the Doppler-mode processing unit 5 may detect Doppler-mode signals based on the one ultrasound data signal. The Doppler-mode processing unit 5 may include a reference signal generator 20, a $\pi/2$ phase shifter 21, mixers 22-1 and 22-2, low-pass filters 23-1 and 23-2, A/D converters 24-1 and 24-2, a Doppler signal memory 25, a moving target indicator filter (hereinafter referred to as an MTI filter) 26, an autocorrelation unit 27, and a calculator 28. The Doppler-mode processing unit 5 mainly performs a quadrature demodulation and a frequency analysis on the one ultrasound data signal.

The one ultrasound data signal is input to a first input terminal of the mixer 22-1 and also to a first input terminal of the mixer 22-2. The reference signal generator 20 has a frequency, which is nearly the same as a center frequency of the one ultrasound data signal. The reference signal generator 20 outputs the reference signal, which is directly supplied to a second terminal of the mixer 22-1. The reference signal is formed of a continuous wave and is synchronized with the rate pulses generated by the rate pulse generator 11. The reference signal is also supplied to the $\pi/2$ phase shifter 21. The $\pi/2$ phase shifter 21 shifts a phase of the reference signal and supplies a second terminal of the mixer 22-2 with a $\pi/2$ shifted reference signal. Output signals of the mixers 22-1 and 22-2 are supplied to the low-pass filters 23-1 and 23-2. The low-pass filter 23-1 removes a sum component of between a frequency of the reference signal and a frequency of the one ultrasound data signal. Accordingly, a differential component of between the frequency of the reference signal and the frequency of the one ultrasound data signal is extracted by the low-pass filter 23-1. Similarly, the low-pass filter 23-2 removes a sum component of between a frequency of the $\pi/2$ shifted reference signal and the frequency of the one ultrasound data signal. Accordingly, a differential component of between the frequency of the $\pi/2$ shifted reference signal and the frequency of the one ultrasound data signal is extracted by the low-pass filter 23-2.

The A/D converter 24-1 converts an output signal of the low-pass filter 23-1 into a digital signal. Similarly, the A/D converter 24-2 converts an output signal of the low-pass filter 23-2 into a digital signal. In other words, output analog signals resulting from a quadrature demodulation are converted into digital signals by the A/D converters 24-1 and 24-2. The digitized output signals (Doppler-mode signals) resulting from the quadrature demodulation are temporarily stored in the Doppler signal memory 25. The MTI filter 26 is a digital high pass filter. The MTI filter 26 reads out the stored Doppler-mode signals from the Doppler signal memory 25 and removes a component (or a clutter component) originating from a respiratory movement and/or a pulsant movement of an organ from the Doppler-mode signals. The autocorrelation unit 27 calculates autocorrelation values of the Doppler-mode signals including only blood flow information extracted by the MTI filter 26. The calculator 28 calculates averaged flow values and dispersion values based on the autocorrelation values.

Also, the image processing unit 6 may produce B-mode image data and Doppler-mode image data based on the B-mode signals and the Doppler-mode signals, respectively, and stores the B-mode image data and the Doppler-mode image data. The image processing unit 6 may also perform processing among these image data. The image processing unit 6 may include a memory 29, a processor 30, and a display memory 31. The memory 29 may sequentially store B-mode signals supplied from the B-mode processing unit 4 and the Doppler-mode signals supplied from the Doppler-mode processing unit 5. The memory 29 may also produce B-mode image data and Doppler-mode image data based on the stored signals and store the produced image data. The processor 30 may conduct a weighting addition on a plurality of the B-mode image data or the Doppler-mode image data and a synthesis processing between the B-mode image data and the Doppler-mode image data. The display memory 31 may temporarily store image data not-processed in the processor 30 and to be displayed in the display unit 8. The display memory 31 may also add (or overlay) supplementary information such as, for example, numeral and/or character information input from the input unit 7 to the image data processed in the processor 30 and store the image data with the supplementary information.

In the embodiment shown in FIG. 2, the input unit 7 may have a keyboard, a trackball, a mouse, and the like, on an operation panel. The operator may operate the input unit 7 so as to input or select patient information, imaging (or scanning) conditions of the ultrasound diagnosis apparatus, and/or various types of commands.

The display unit 8 may include a converter 32 and a monitor 33. The monitor 33 may include a CRT (cathode ray tube) monitor or an LCD (liquid crystal display) and display in color. The converter 32 may implement a digital to analog (D/A) conversion and TV formatting conversion on the B-mode image data and the Doppler-mode image data stored in the display memory 31. The converter 32 may also implement coloring processing on the Doppler-mode image data. The converted image data may be displayed in the monitor 33.

The system control unit 9 may typically include a central processing unit (CPU) (not shown in FIG. 2) and a CPU memory (not shown in FIG. 2). The system control unit 9 may temporarily store the various types of data and commands input from the input unit 7 in the CPU memory. The system control unit 9 may also control the ultrasound transmission unit 2, the ultrasound reception unit 3, the B-mode processing unit 4, the Doppler-mode processing unit 5, the image processing unit 6, and the like based on the data and the commands. The system control unit 9 may also control over the ultrasound diagnosis apparatus based on the data and the commands.

Figure 3:
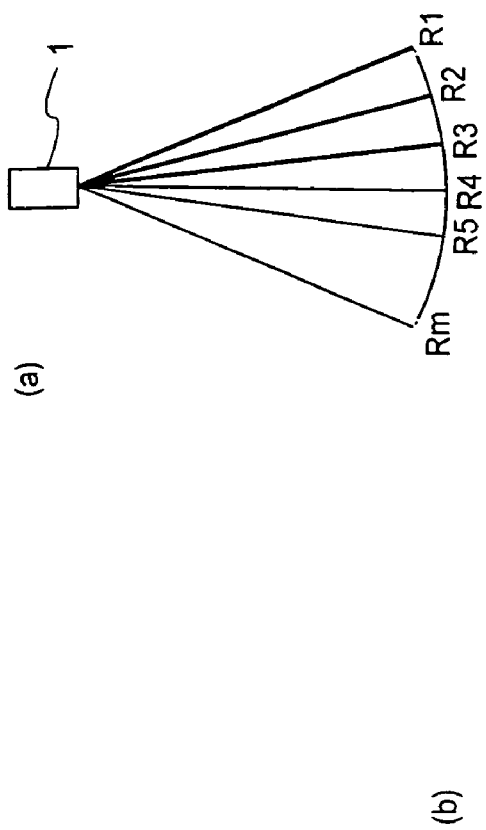
FIG. 3 is an illustration for explaining an exemplary interleaving scan technique.
Figure 3:
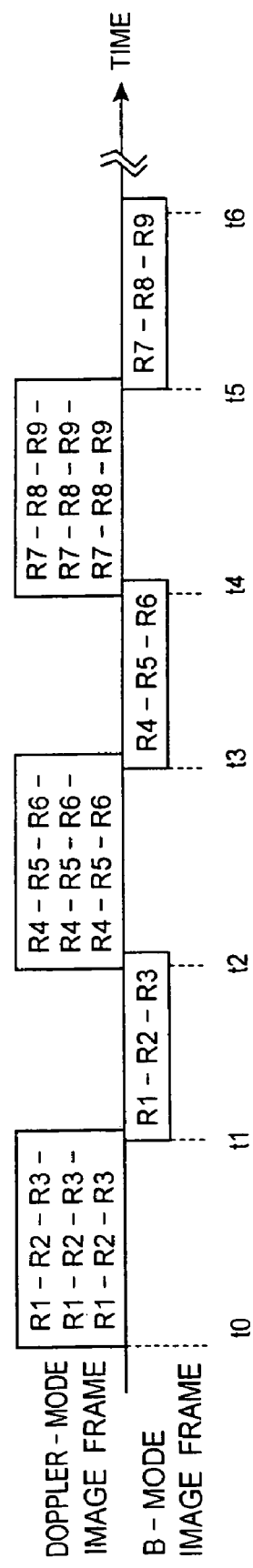

Next, an example of an interleaving scan technique will be described with reference to FIG. 3. FIG. 3 is an illustration for explaining an exemplary interleaving scan technique. The interleaving scan shown in FIG. 3 regards of a case when Doppler-mode signals and B-mode signals are acquired. As shown in FIR. 3, the number of raster directions is 3 (Q=3) This is only for the purpose of explanation and the number Q of raster directions is not limited to three but may be any number. In practice, the Q may be determined to be, for example, between 8 and 16. The number of sets of ultrasound transmission and reception in each of the raster directions is 3 (n=3). This is also only for the purpose of explanation and the n is not limited to three but may be any number. In practice, the n may be determined to be, for example, between 12 and 16.

The ultrasound transmission and reception are conducted in the raster direction R1 and continues at the rate interval Tr in the order of R2, R3, R1, R2, R3, R1, R2, and R3. Accordingly, Doppler-mode signals are acquired and stored based on the ultrasound transmission and reception in the raster directions R1 to R3. After the acquisition and transmission of Doppler-mode signals in a group of the raster directions R1 to R3, the ultrasound transmission and reception are then conducted to acquire B-mode signals in a group of the raster directions R1 to R3. For B-mode signals, the ultrasound transmission and reception is conducted only once in each raster direction. Accordingly, B-mode signals are acquired and stored based on the ultrasound transmission and reception in the raster directions R1 to R3. The ultrasound transmission and reception conducted to acquire B-mode signals may be called a B-mode scan in embodiments of the present invention. After the acquisition and storage of B-mode signals in a group of the raster directions R1 to R3, the acquisition and storage are conducted for each group of the raster directions R4 to R6, R7 to R9, and so on until the raster direction Rm, with respect to the Doppler-mode signals and the B-mode signals. Based on the acquisition and storage of the Doppler-mode signals in the raster directions R1 to Rm, one Doppler-mode image frame is prepared. Similarly, based on the acquisition and storage of the B-mode signals in the raster directions R1 to Rm, one B-mode image frame is prepared. A plurality of Doppler-mode image frames may be prepared as the Doppler-mode image data. Also, a plurality of B-mode image frames may be prepared as the B-mode image data.

The operator may operate the input unit 7 so as to input patient information and set operating conditions of the ultrasound diagnosis apparatus. The input information and set conditions are stored in the memory provided in the system control unit 9. The operator then selects a display mode so that both or one of Doppler-mode images and B-mode images are displayed. When the operator selects a display mode corresponding to a display of both the Doppler-mode images and the B-mode images, the operator also inputs commands with respect to such a display.

In response to the operator's operation, the system control unit 9 receives the commands from the input unit 7. The system control unit 9 then supplies control signals to various components of the ultrasound diagnosis apparatus. The various components start operations for acquiring Doppler-mode signals and B-mode signals in the raster directions R1 to R3 included in the first group when the raster directions R1 to Rm are divided into a plurality of groups.

In the transmission in the raster direction R1, the rate pulse generator 11 synchronizes control signals supplied from the system control unit 9. The rate pulse generator 11 generates rate pulses, which determine a repetition cycle (the rate interval Tr) of the ultrasound pulses insonified to the patient body. The generated rate pulses are supplied to the transmission delay circuit 12. The transmission delay circuit 12 is a delay circuitry, which determines a convergent distance and a deflecting angle of an ultrasound beam in transmission. Further, the transmission delay circuit 12 may include a plurality of independent delay circuits. The number of the independent delay circuits to be used may be determined to be the same as that of the transducers to be used in transmission. The transmission delay circuit 12 provides the generated rate pulses with a delay time for making the ultrasound pulses converge to a predetermined depth. This is for obtaining an arrow width of the ultrasound beam in transmission. The transmission delay circuit 12 further provides the generated rate pulses with another delay time for transmitting the ultrasound pulses in the first raster direction R1.

The pulsar 13 may include a plurality of independent driving circuits. The number of the independent driving circuits to be used may be determined to be the same as that of the transducers to be used in the transmission as similar to the transmission delay circuit 12. The pulsar 13 produces driving signals for driving the transducers responsive to driving rate pulses, and drives the transducers. Accordingly, the ultrasound pulses are insonified in the raster direction R1 in the patient body. Part of the ultrasound pulses insonified to the patient body usually reflects off tissues or borders between organs within the patient body, where their acoustic impedances are different. Further, when the part of the ultrasound pulses reflects off moving reflectors, such as blood cells and heart walls, its ultrasound frequencies are subjected to Doppler-shifts.

The ultrasound pulses reflected off the tissues of the patient body may be received as the echo signals by the transducers. The received echo signals are converted into electronic signals. The converted electronic signals are amplified by the preamplifier 14. The preamplifier 14 may include a plurality of channels. The number of the channels to be used may be determined to be the same as that of the transducers to be used in the reception. The amplified signals are received by the reception delay circuit 15.

The reception delay circuit 15 gives the received signals a delay time for converging the echo signals from a predetermined depth (the received signals) so as to obtain a narrow width of an ultrasound beam in reception. The reception delay circuit 15 further gives the received signals another delay time for receiving the ultrasound beam with strong directional characteristics in the raster direction R1. The reception delay circuit 15 supplies the adder 16 with the received signals given both the above delay time and the above another delay time. The received signals are supplied to the adder 16 from the reception delay circuit 15. The adder 16 adds (or unifies) a plurality of the received signals supplied through the preamplifier 14 and the reception delay circuit 15. Accordingly, the plurality of the received signals are output to the Doppler-mode processing unit 5 as one ultrasound data signal.

The system control unit 9 controls the Doppler-mode processing unit 5 to process the one ultrasound data signal. In the Doppler-mode processing unit 5, complex signals are produced as a result of the quadrature demodulation. The complex signals are converted into digital signals and stored in the Doppler signal memory 25.

Figure 4:
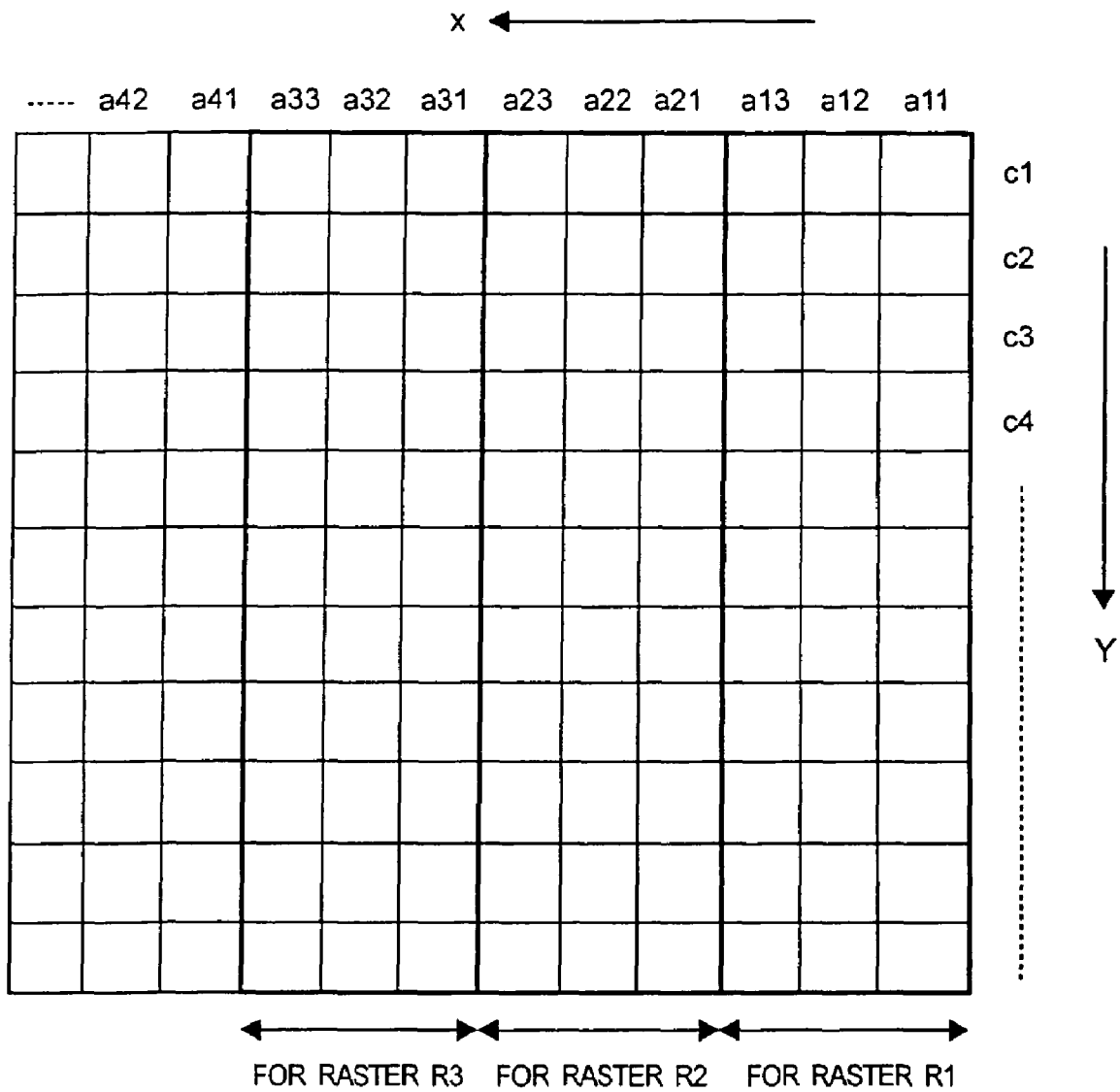
FIG. 4 is an illustration for explaining an exemplary Doppler signal memory.

FIG. 4 is an illustration for explaining the Doppler signal memory 25. FIG. 4 shows only one example of a memory format included in the Doppler signal memory 25. The memory format is formed of a matrix. The row direction (X direction) of the matrix shows raster directions R1 to Rm or the number of times (n) of the ultrasound transmission and reception in each raster direction. The column direction (Y direction) of the matrix shows depth ($c_1$, $c_2$, $c_3$, etc.) of a reflector (i.e., a distance between the reflector and the ultrasound probe 1). For example, Doppler-mode signals acquired by the first ultrasound transmission and reception in the raster direction R1 are stored in a column $a_{11}$. To be precise, the Doppler-mode signals acquired by the first ultrasound transmission and reception in the raster direction R1 are converted into digital signals by the A/D converter 24-1 and 24-2, and the digital signals are stored in the column $a_{11}$. Similarly, columns $a_{12}$ and $a_{13}$ correspond to the second and third ultrasound transmission and reception in the raster direction R1, respectively. Doppler-mode signals acquired by the first to third ultrasound transmission and reception in the raster direction R2 are stored in columns $a_{21}$ to $a_{23}$, respectively. Doppler-mode signals acquired by the first to third ultrasound transmission and reception in the raster direction R3 are stored in columns $a_{31}$ to $a_{33}$, respectively.

Meanwhile, after the first ultrasound transmission and reception in the raster direction R1, the system control unit 9 supplies control signals to the transmission delay circuit 12 and the reception delay circuit 15 so as to determine a delay time for the ultrasound transmission and reception in the raster direction R2. Similarly, after the first ultrasound transmission and reception in the raster direction R2, the system control unit 9 supplies control signals to the transmission delay circuit 12 and the reception delay circuit 15 so as to determine a delay time for the ultrasound transmission and reception in the raster direction R3. As described above, Doppler signals acquired by the first ultrasound transmission and reception in the raster directions R1 to R3 are stored in the columns $a_{11}$, $a_{21}$, and $a_{31}$. When the first ultrasound transmission and reception in the raster directions R1 to R3 have been completed, the second and third ultrasound transmission and reception in the raster directions R1 to R3 are repeated so that Doppler-mode signals acquired by the second and third ultrasound transmission and reception are stored in the columns $a_{12}$, $a_{22}$, and $a_{32}$, and the columns $a_{13}$, $a_{23}$, and $a_{33}$.

The Doppler-mode signals stored in the Doppler signal memory 25 are read out and supplied to the MTI filter 26. For example, the Doppler-mode signals stored for the raster direction R1 are read out from a depth $c_1$ in the order of $a_{11}$, $a_{12}$, and $a_{13}$. In the MTI filter 26, clutter component information originating from a respiratory movement and the like of an organ is removed from the Doppler-mode signals so that only blood flow component information is extracted. The autocorrelation unit 27 calculates autocorrelation values of the Doppler-mode signals including only blood flow component information. The calculator 28 calculates, for example, averaged flow values, dispersion values, and power values with respect to blood flows based on the autocorrelation values. Similar processing to the above description may be repeated on the Doppler signals read out from depths $c_2$, $c_3$, and so on. The calculated blood flow information of the Doppler signals acquired in the raster direction R1 is stored in a color Doppler field provided in the memory 29.

Regarding the raster direction R2, the Doppler-mode signals stored in the columns $a_{12}$, $a_{22}$, and $a_{32}$ of the Doppler signal memory 25 are read out and processed in a manner similar to the above case of the raster direction R1. Also, regarding the raster direction R3, the Doppler-mode signals stored in the columns a13, a23, and a33 of the Doppler signal memory 25 are read out and processed in a manner similar to the above case of the raster direction R1. Calculated blood flow information of the Doppler signals acquired in the raster directions R2 and R3 is also stored in the color Doppler field provided in the memory 29.

As described above, when the acquisition and storage of the Doppler-mode signals have been completed based on the three-time interleaving scan in the raster directions R1 to R3, acquisition and storage of the B-mode signals will be conducted in the raster directions R1 to R3.

The system control unit 8 controls the ultrasound transmission unit 2 and the ultrasound reception unit 3 to conduct the ultrasound transmission and reception in the raster direction R1. The received signals output from the adder 16 provided in the ultrasound reception unit 3 are supplied to the logarithmic transformer 17. The received signals are logarithmically transformed by the logarithmic transformer 17 and then detected their envelopes by the envelope detector 18. The envelop-detected signals are converted into digital signals by the A/D converter 19. The digital signals are stored in a B-mode field provided in the memory 29 as B-mode signals. After the raster direction R1, similar acquisition and storage are conducted in the raster directions R2 and R3.

Accordingly, the acquisition and storage of the Doppler-mode signals and the B-mode signals based on the ultrasound transmission and reception in the raster directions R1 to R3 are completed. Similar acquisition and storage are conducted based on the ultrasound transmission and reception in the raster directions R4 to R6 included in each of the second group of the first Doppler-mode image frame and the second group of the first B-mode image frame. Further, similar acquisition and storage may be repeated in the raster directions R7 to R9 included in the third group, the raster directions R10 to R12 included in the fourth group, and so on.

When the acquisition and storage of the Doppler-mode signals and the B-mode signals for the first Doppler-mode image frame and the first B-mode image frame have been conducted, the ultrasound transmission and reception will continue for the second Doppler-mode image frame and the second B-mode image frame, and so on. However, ultrasound transmission and reception for the further image frames than the first image frame will be controlled, for example, in a manner shown in FIGS. 5 and 6.

Figure 5:
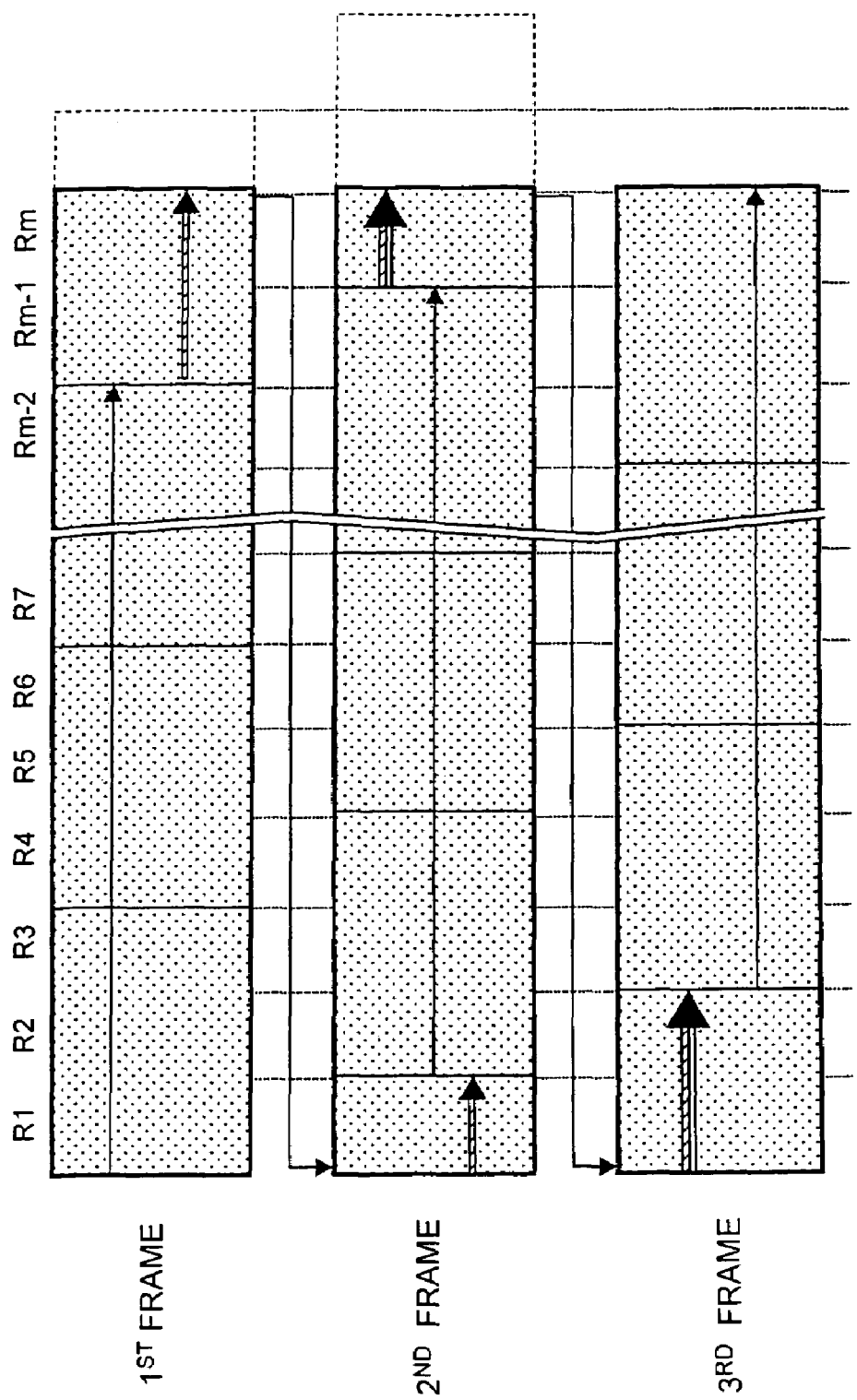
FIG. 5 is an illustration showing an example of an ultrasound scanning control according to the first embodiment of the present invention.
Figure 6:
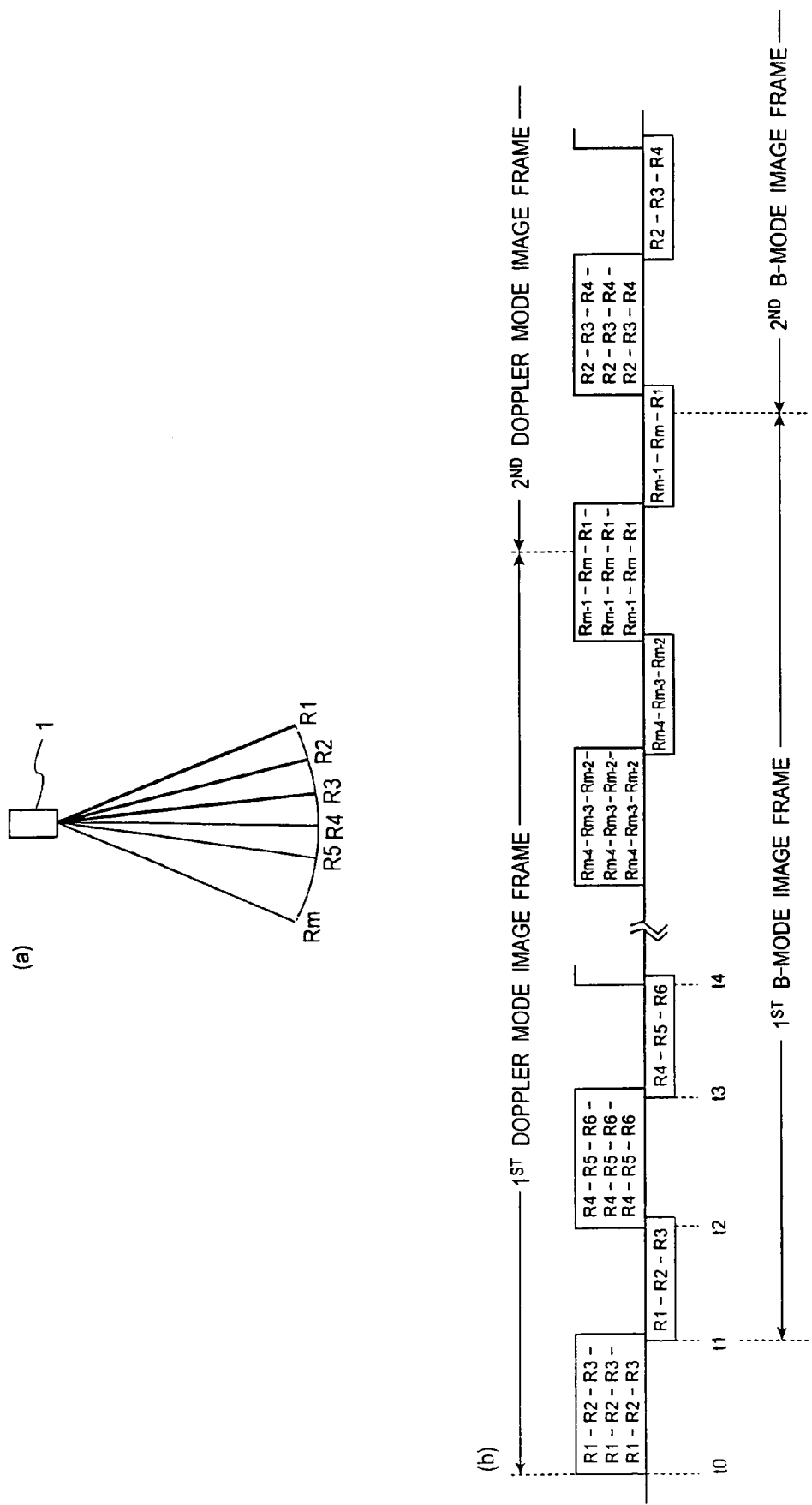
FIG. 6 is an illustration showing an example of a time chart for describing the scanning control shown in FIG. 5 according to the first embodiment of the present invention.

FIG. 5 is an illustration showing an example of an ultrasound scanning control according to the first embodiment. FIG. 6 is an illustration showing an example of a time chart for describing the ultrasound scanning control shown in FIG. 5 according to the first embodiment. FIG. 5 shows the first to third Doppler-mode image frames each of which being acquired by the ultrasound transmission and reception in the raster directions R1 to Rm. This is a case that the number (m) of the raster directions is divided by the Q (e.g., Q=3) and there is a remainder. In FIG. 5, the last group of the raster directions includes only two raster directions while others include three each. For example, the first group includes the raster directions R1 to R3. The second group includes the raster directions R4 to R6. The above-described acquisition and storage in the raster directions R1 to R3 are conducted in a time period corresponding to the first group shown in FIG. 5. Although not shown in FIG. 5, the acquisition and storage of the B-mode signals in the raster directions R1 to R3 are conducted in a time period between the first group and the second group of the Doppler-mode image frame.

For the first Doppler-mode image frame, the acquisition and storage are repeated in every group of from the first group until a group before the last including the raster directions Rm-4 to Rm-2. Since the last group of the first Doppler-mode image frame includes only the raster directions Rm-1 and Rm, the first raster direction R1 for the second Doppler-mode image frame is treated as a part of the last group of the first Doppler-mode image frame. That is, the acquisition and storage in the first raster direction R1 included in the first group of the second Doppler-mode image frame is conducted as a part of the last group of the first Doppler-mode image frame. Therefore, after the first acquisition and storage have been conducted in the raster directions Rm-1 and Rm, the acquisition and storage continue in the first raster direction R1. Similarly, the second and third acquisition and storage are conducted within the group including the raster directions Rm-1, Rm, and R1. After the three-time acquisition and storage of the Doppler-mode signals in the raster directions Rm-1, Rm, and R1, the acquisition and storage of the B-mode signals are conducted within a group including the raster directions Rm-1, Rm, and R1.

After the acquisition and storage of the B-mode signals in the raster directions Rm-1, Rm, and R1, the acquisition and storage are conducted within the second group including the raster directions R2 to R4 for the second Doppler-mode image frame. Also similar acquisition and storage are repeated until a group before the last including the raster directions Rm-3 to Rm-1. This time, the last group of the second Doppler-mode image frame includes only the raster direction Rm. Therefore, the first and second raster directions R1 and R2 included in the first group of the third Doppler-mode image frame are treated as a part of the last group of the second Doppler-mode image frame. That is, the acquisition and storage in the first and second raster directions R1 and R2 included in the first group of the third Doppler-mode image frame is conducted as a part of the last group of the second Doppler-mode image frame. Therefore, after the first acquisition and storage have been conducted in the raster direction Rm, the acquisition and storage are then conducted in the first and second raster directions R1 and R2. Similarly, the second and third acquisition and storage are conducted within the group including the raster directions Rm, R1, and R2. After the three-time acquisition and storage of the Doppler-mode signals in the raster directions Rm, R1, and R2, the acquisition and storage of the B-mode signals are conducted within a group including the raster directions Rm, R1, and R2. After the acquisition and storage of the B-mode signals in the raster directions Rm, R1, and R2, the acquisition and storage are conducted within the second group including the raster directions R3 to R5 for the third Doppler-mode image frame. Also similar acquisition and storage are repeated until the last group including the raster directions Rm-2 to Rm.

Similar acquisition and storage based on the ultrasound transmission and reception control (scanning control) described above may be applied to other Doppler-mode image frames and B-mode image frames. For example, the scanning control will be conducted among the fourth to sixth Doppler-mode image frames (B-mode image frames), among the seventh to ninth Doppler-mode image frames (B-mode image frames), and so on. The Doppler-mode signals and B-mode signals acquired by the ultrasound transmission and reception for those frames may also be stored in the memory 29.

Each Doppler-mode image frame may be prepared based on the stored Doppler-mode signals acquired by the ultrasound transmission and reception in the raster directions R1 to Rm for the Doppler-mode image frame. Also, each B-mode image frame may be prepared based on the stored B-mode signals acquired by the ultrasound transmission and reception in the raster directions R1 to Rm for the B-mode image frame.

Due to the motion of an object to be examined (i.e., a moving reflector), boundary discontinuity may appear in each of the Doppler-mode image frames and the B-mode image frames. The discontinuity originates from a time phase difference between the acquisition of one group and the next, and each image frame includes a plurality of the groups. For example, such discontinuity may appear at positions of the first image frame between, for example, the raster directions R3 and R4, and R6 and R7. Also, such discontinuity may appear at positions of the second image frame between, for example, the raster directions R1 and R2, and R4 and R5. However, a plurality of the Doppler-mode image frames (the B-mode image frames) are usually displayed continuously like a moving picture. Since the boundaries are present at different positions among the image frames, the discontinuity may become indistinctive when the plurality of the Doppler-mode image frames (the B-mode image frames) are displayed as ultrasound images.

A single Doppler-mode image frame (a single B-mode image frame) is sometimes displayed as a freeze-image. In such a case, if the image frame includes discontinuity, the discontinuity may be recognizable by the operator. In order to reduce such discontinuity, a weighting addition technique may be applied to the Doppler-mode image frame (the B-mode image frame). This technique may also be advantageous for a better continuous display of a plurality of the Doppler-mode image frames (the B-mode image frames).

Figure 7:
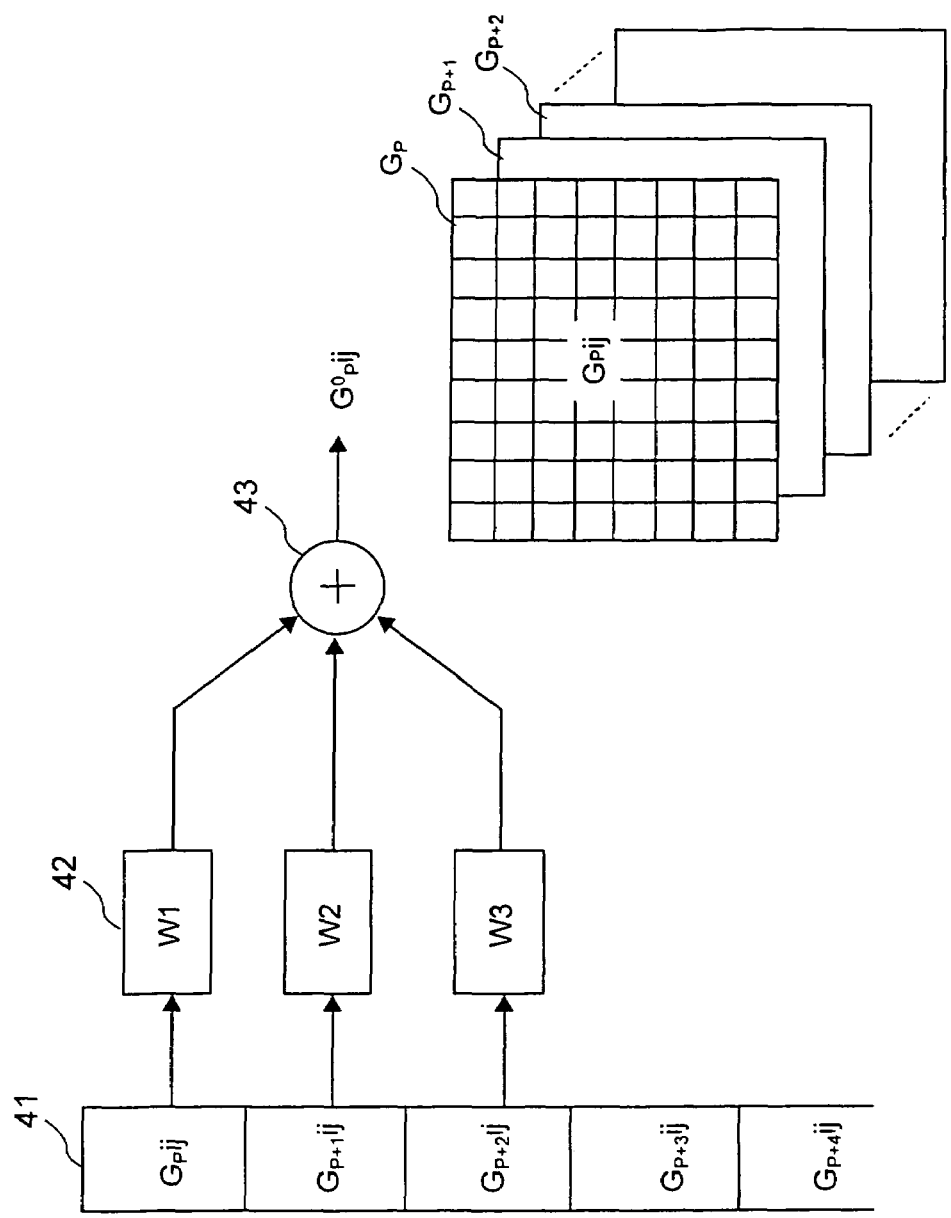
FIG. 7 is an illustration showing an example of a weighting addition among a plurality of Doppler-mode image frames according to the first embodiment of the present invention.

FIG. 7 is an illustration showing an example of a weighting addition among a plurality of Doppler-mode image frames according to the first embodiment. The processor 30 sequentially reads out a plurality of the prepared Doppler-mode image frames from the memory 29. The processor 30 conducts an image calculation processing among the Doppler-mode image frames. The processor 30 may include a shift register 41, a weighting unit 42, and an adder 43. Functions accomplished by these components may alternatively realized by a software. In FIG. 7, Doppler-mode image frames Gp to Gp+4 are shown as examples of the Doppler-mode image frames. A pixel of the Doppler-mode image frame Gp is expressed as Gpij. The 'i' represents a row of a two-dimensional image matrix. The 'j' represents a column of the two-dimensional image matrix. Corresponding pixels of the Doppler-mode image frames Gpij, Gp+1ij, Gp+2ij, Gp+3ij, Gp+4ij, and the like are read out to the shift register 41. The weighting unit 42 weights on, for example, the pixels Gpij, Gp+1ij, and Gp+2ij. The number of pixels to be used for the weighting is not limited to three. Any plurality of pixels may be used for the weighting. In other words, the number of image frames to be used for the weighting is not limited to three. Any plurality of image frames may be used for the weighting. These weighted pixels Gpij, Gp+1ij, and Gp+2ij are added by the adder 43 and output as a weighted pixel Gopij. Therefore, the weighted pixel Gopij may be used for a display instead of the pixel Gpij.

In the weighting application, the pixels Gpij, Gp+1ij, and Gp+2ij maybe averaged. In another example, the pixel Gpij may be given a highest weighting proportion W1 (e.g., 0.6). Other weighting proportions W2 and W3 for the pixels Gp+1ij and Gp+2ij may be, for example, 0.3 and 0.1. The proportions may be predetermined or determined by the operator. Further, the pixels to be applied to the weighting may be limited to pixels located around the boundaries, instead of all the pixels included in the Doppler-mode image frame. The weighted pixel Gopij may be expressed by the following formula.

$$Gopij = W1*Gpij + W2*Gp+1ij + W3*Gp+2ij$$

Therefore, for example, a weighted pixel Gop+1ij may be obtained from the pixels Gp+1ij, Gp+2ij, and Gp+3ij.

The above weighting technique may also be applied to a plurality of the prepared B-mode image frames.

The Doppler-mode image frames added the weighting and the B-mode image frames added the weighting are independently stored in the memory 29. In addition or alternatively, the Doppler-mode image frames added the weighting and the B-mode image frames added the weighting may be synthesized and stored in a synthesized form in the memory 29.

When the Doppler-mode image frames with or without the weighting addition and/or the B-mode image frames with or without the weighting addition are displayed in the monitor 33, the system control unit 9 controls the display memory 31 to add (or overlay) the supplementary information to the image frames. The image frames with the supplementary information are stored as image data in the display memory 31. The converter 32 implements, for example, the D/A conversion and the TV formatting conversion on the image data. When the image data regard of the Doppler-mode, the converter 32 may also implement the coloring processing on the image data. The converted image data are displayed in the monitor 33.

Second Embodiment

This is an embodiment that the number (m) of the raster directions is divided by the Q (e.g., Q=3) and a remainder is zero.

Figure 8:
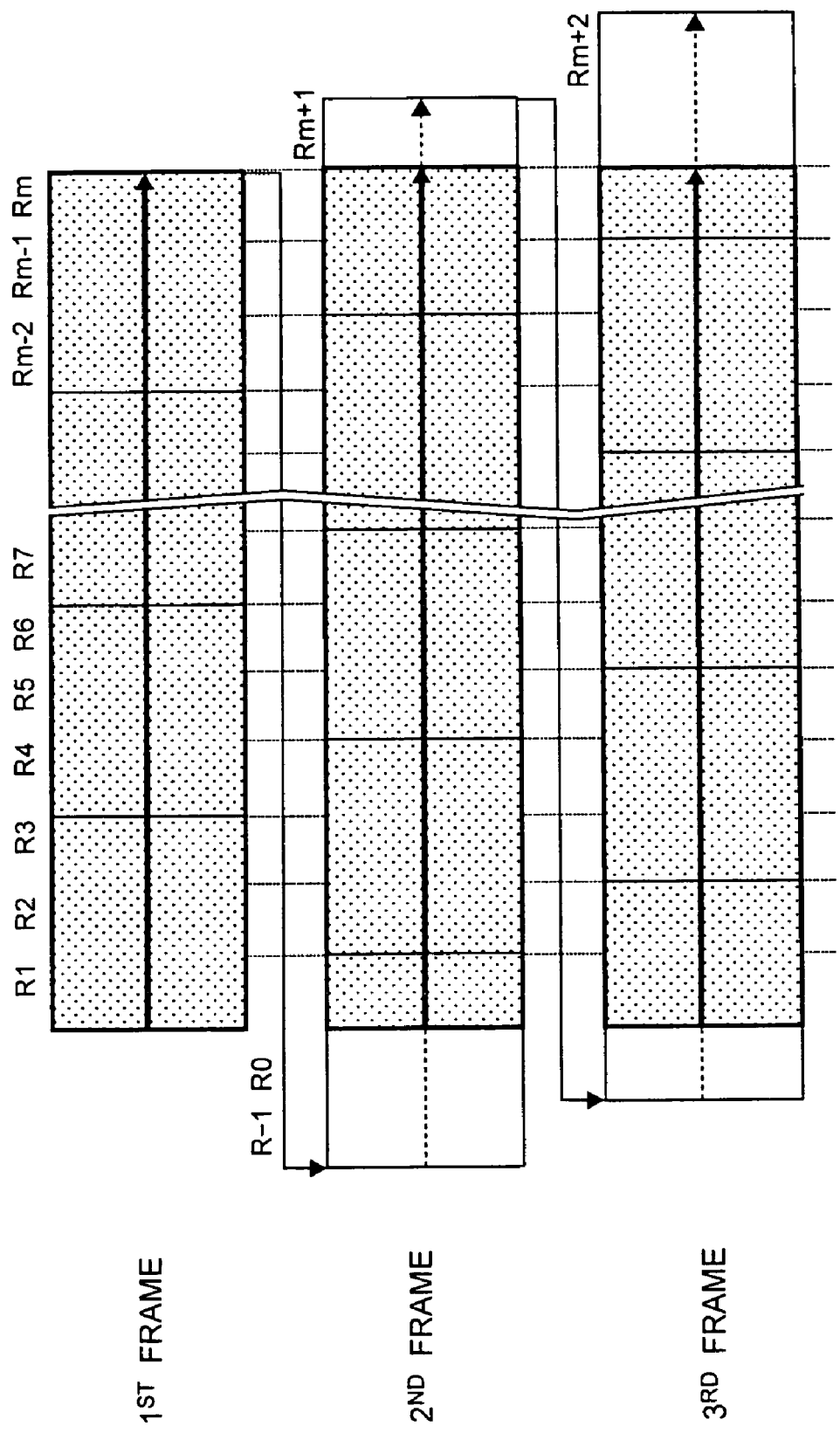
FIG. 8 is an illustration showing an example of an ultrasound scanning control according to the second embodiment of the present invention.
Figure 9:
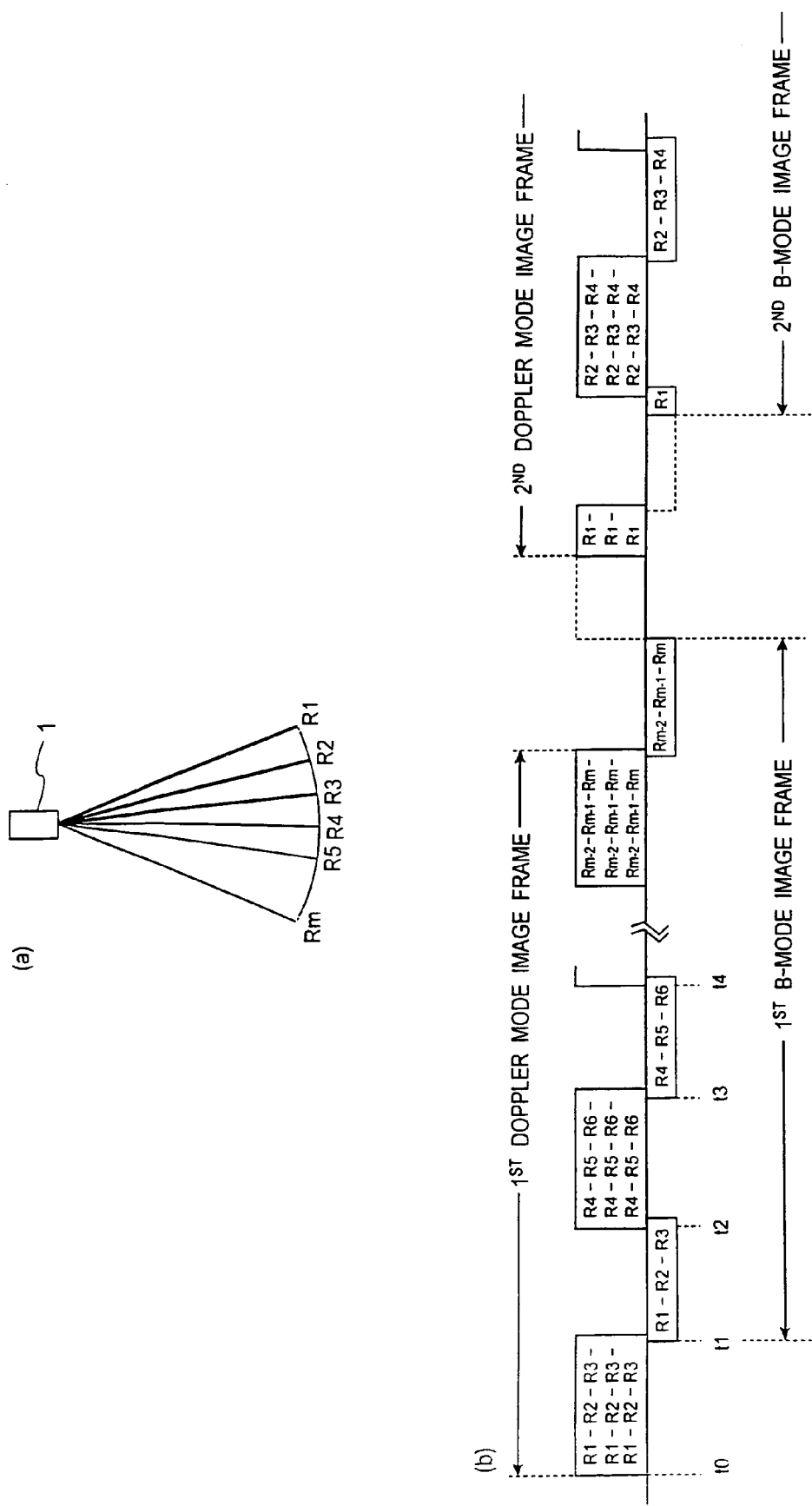
FIG. 9 is an illustration showing an example of a time chart for describing the ultrasound scanning control shown in FIG. 8 according to the second embodiment of the present invention.
Figure 10:
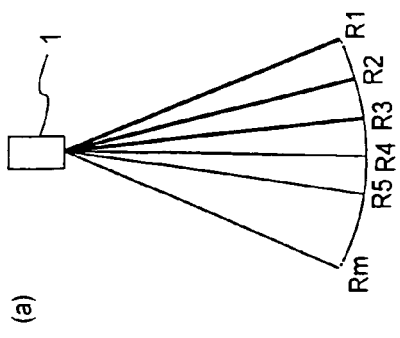
FIG. 10 is an illustration showing another example of a time chart for describing the ultrasound scanning control shown in FIG. 8 according to the second embodiment of the present invention.
Figure 10:
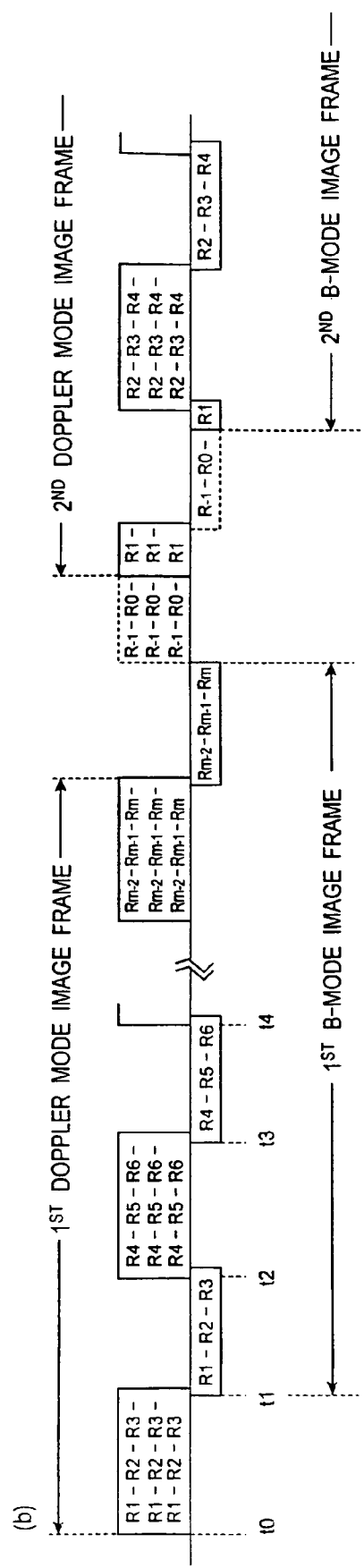

FIG. 8 is an illustration showing an example of an ultrasound scanning control according to the second embodiment. FIG. 9 is an illustration showing an example of a time chart for describing the ultrasound scanning control shown in FIG. 8 according to the second embodiment. Further, FIG. 10 is an illustration showing another example of a time chart for describing the ultrasound scanning control shown in FIG. 8 according to the second embodiment. FIG. 8 shows the first to third Doppler-mode image frames each of which being acquired by the ultrasound transmission and reception in the raster directions R1 to Rm. The number (m) of the raster directions may be intentionally determined to be a number which can be divided by the Q without a remainder. Therefore, the last group of the raster directions in the first Doppler-mode image frame includes three raster directions Rm-2, Rm-1, and Rm like other groups of the raster directions in the first Doppler-mode image frame. Similar to the first embodiment, the first group of the first Doppler-mode image frame includes the raster directions R1 to R3. The second group includes the raster directions R4 to R6. The acquisition and storage in the raster directions R1 to R3 for the B-mode image frame are conducted in a time period between the first group and the second group of the first Doppler-mode image frame. The acquisition and storage of the B-mode signals are conducted in every period between two adjacent groups of the Doppler-mode image frame.

After the acquisition and storage in the last group of the first Doppler-mode image frame, the acquisition and storage of the B-mode signals are conducted for the last group of the first B-mode image frame including the raster directions Rm-2 to Rm. As shown in FIG. 9, the acquisition and storage are then controlled to stop for a predetermined time period (a first break period). This first break period corresponds to a time period to be spent or required for, for example, the acquisition and storage in two raster directions. After the first break period, the acquisition and storage restart in the raster direction R1 included in the first group of the second Doppler-mode image frame. Also in the second and third turns, the above first break period and the acquisition and storage in the raster direction R1 are repeated. After the acquisition and storage has been completed in the raster direction R1 for the second Doppler-mode image frame, the acquisition and storage are controlled again to stop for a predetermined time period (a second break period) corresponding to a time period to be spent or required for, for example, the B-mode signal acquisition and storage in two raster directions. After the second break period, the acquisition and storage restart in the raster direction R1 included in the first group of the second B-mode image frame.

After the acquisition and storage of the B-mode signals in the raster direction R1, the acquisition and storage are conducted within the second group including the raster directions R2 to R4 for the second Doppler-mode image frame. Also similar acquisition and storage are repeated until a group before the last including the raster directions Rm-4 to Rm-2. This time, the last group of the second Doppler-mode image frame includes only the raster directions Rm-1 and Rm. In this last group, the acquisition and storage in the raster directions Rm-1 and Rm are conducted as the first time acquisition and storage. The acquisition and storage are then controlled to stop for a predetermined time period (a third break time) corresponding to a time period to be spent or required for, for example, the acquisition and storage in one raster direction. After the third break period, the acquisition and storage restart in the raster directions Rm-1 and Rm. Also in the second and third turn, the acquisition and storage in the raster directions Rm-1 and Rm and the above third break period are repeated.

After the last third break period has passed, the acquisition and storage of the B-mode signals are conducted. Similar to the control of the second Doppler-mode image frame, the acquisition and storage in the raster directions Rm-1 and Rm are conducted for the last group of the second B-mode image frame. The acquisition and storage are then controlled to stop for a predetermined time period (a fourth break period) corresponding to a time period to be spent or required for, for example, the B-mode signal acquisition and storage in one raster direction.

Even after the fourth break period relating to the last group of the second B-mode image frame, the acquisition and storage are still controlled to stop for a predetermined time period (a fifth break period) corresponding to a time period to be spent or required for, for example, the acquisition and storage in one raster direction. When the fifth break period has passed, the acquisition and storage restart in the raster directions R1 and R2 included in the first group of the third Doppler-mode image frame. Also in the second and third turn, the above fifth break period and the acquisition and storage in the raster directions R1 and R2 are repeated. After the acquisition and storage has been completed in the raster directions R1 and R2 for the third Doppler-mode image frame, the acquisition and storage are controlled again to stop for a predetermined time period (a sixth break period) corresponding to a time period to be spent or required for, for example, the B-mode signal acquisition and storage in one raster direction. After the sixth break period, the acquisition and storage restart in the raster directions R1 and R2 included the first group of the third B-mode image frame.

After the acquisition and storage of the B-mode signals in the raster directions R1 and R2, the acquisition and storage are conducted within the second group including the raster directions R3 to R5 for the second Doppler-mode image frame. Also similar acquisition and storage are repeated until a group before the last including the raster directions Rm-3 to Rm-1. This time, the last group of the third Doppler-mode image frame includes only the raster direction Rm. In this last group, the acquisition and storage in the raster direction Rm are conducted as the first time acquisition and storage. The acquisition and storage are then controlled to stop for a predetermined time period (a seventh break period) corresponding to a time period to be spent or required for, for example, the acquisition and storage in two raster directions. When the seventh break period has passed, the acquisition and storage restart in the raster direction Rm. Also in the second and third turn, the acquisition and storage in the raster direction Rm and the above seventh break period are repeated.

After the last seventh break period has passed, the acquisition and storage of the B-mode signals are conducted. Similar to the control of the third Doppler-mode image frame, the acquisition and storage in the raster direction Rm are conducted for the last group of the third B-mode image frame. The acquisition and storage are then controlled to stop for a predetermined time period (an eighth break period) corresponding to a time period to be spent or required for, for example, the B-mode signal acquisition and storage in two raster directions.

For the following Doppler-mode image frames and B-mode image frames, controls of the acquisition and storage similar to the above may be repeated so as to avoid group boundaries, which may appear in one image frame, from locating at the same positions of boundaries, which may appear in the next image frame.

In the second embodiment, one or more of the break periods may be replaced with dummy acquisition and storage in one or more of raster directions other than the raster directions R1 to Rm as shown in FIGS. 9 and 10.

For example, each of the first and second break periods maybe replaced with the acquisition and storage in raster directions R-1 and R0. Also for example, each of the third and fourth break periods may be replaced with the acquisition and storage in a raster direction Rm+1. Further for example, each of the fifth and sixth break periods may be replaced with the acquisition and storage in the raster direction R0. Still further for example, each of the seventh and eighth break periods may be replaced with the acquisition and storage in the raster direction Rm+1 and a raster direction Rm+2. Doppler-mode signals and B-mode signals acquired in the ultrasound transmission and receptions in the above dummy raster directions maybe invalidated after or even before the storage.

In this exemplary embodiment, each Doppler-mode image frame may be prepared based on the acquisition and storage of the Doppler-node signals acquired by the ultrasound transmission and reception in the raster directions R1 to Rm. The prepared Doppler-mode image frames are displayed in the monitor 33 in a manner similar to the first embodiment. Also each B-mode image frame may be prepared based on the acquisition and storage of the B-mode signals acquired by the ultrasound transmission and reception in the raster directions R1 to Rm. The prepared B-mode image frames are displayed in the monitor 33 in a manner similar to the first embodiment.

According to the second embodiment, the break period or the dummy ultrasound transmission and reception are inserted during a time period between two adjacent image frames. Therefore, the frame frequency may deteriorate, compared to the first embodiment, in the display of the Doppler-mode image frames and/or the B-mode image frames. However, the discontinuity which may appear in each image frame due to a time phase difference between one group and the next of the raster directions is controlled to differ with respect to appearing positions in one image frame and the next. Therefore, when a plurality of the Doppler-mode image frames (a plurality of the B-mode image frames) are continuously displayed in the monitor 33, the discontinuity may become indistinctive as in the first embodiment. The second embodiment may be advantageous since the discontinuity may become indistinctive even when the number of raster directions to be used for the ultrasound transmission and reception can be divided by the Q without a remainder.

The weighting addition described in the first embodiment may also be applied to the second embodiment. The number Q of the raster directions included in each group of the Doppler-mode image frame or the B-mode image frame is not limited to three. Any number of raster directions may be assigned to each group of the Doppler-mode image frame or the B-mode image frame.

Modification

The controls of the acquisition and storage described in the first and second embodiments may be applied to a case that only Doppler-mode image frames are acquired.

Figure 11:
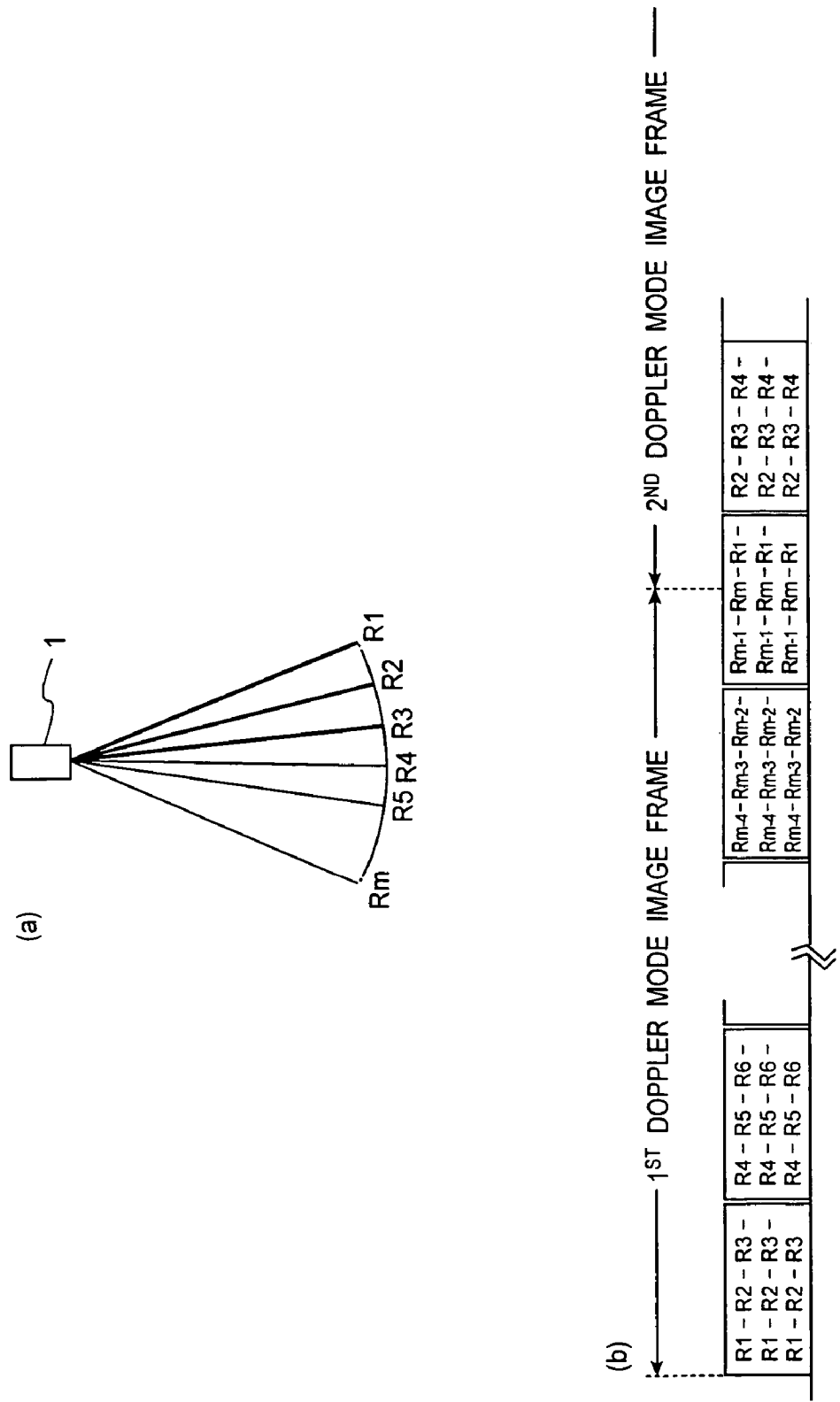
FIG. 11 is an illustration showing an example of a time chart for illustrating a modification to the first embodiment of the present invention.
Figure 12:
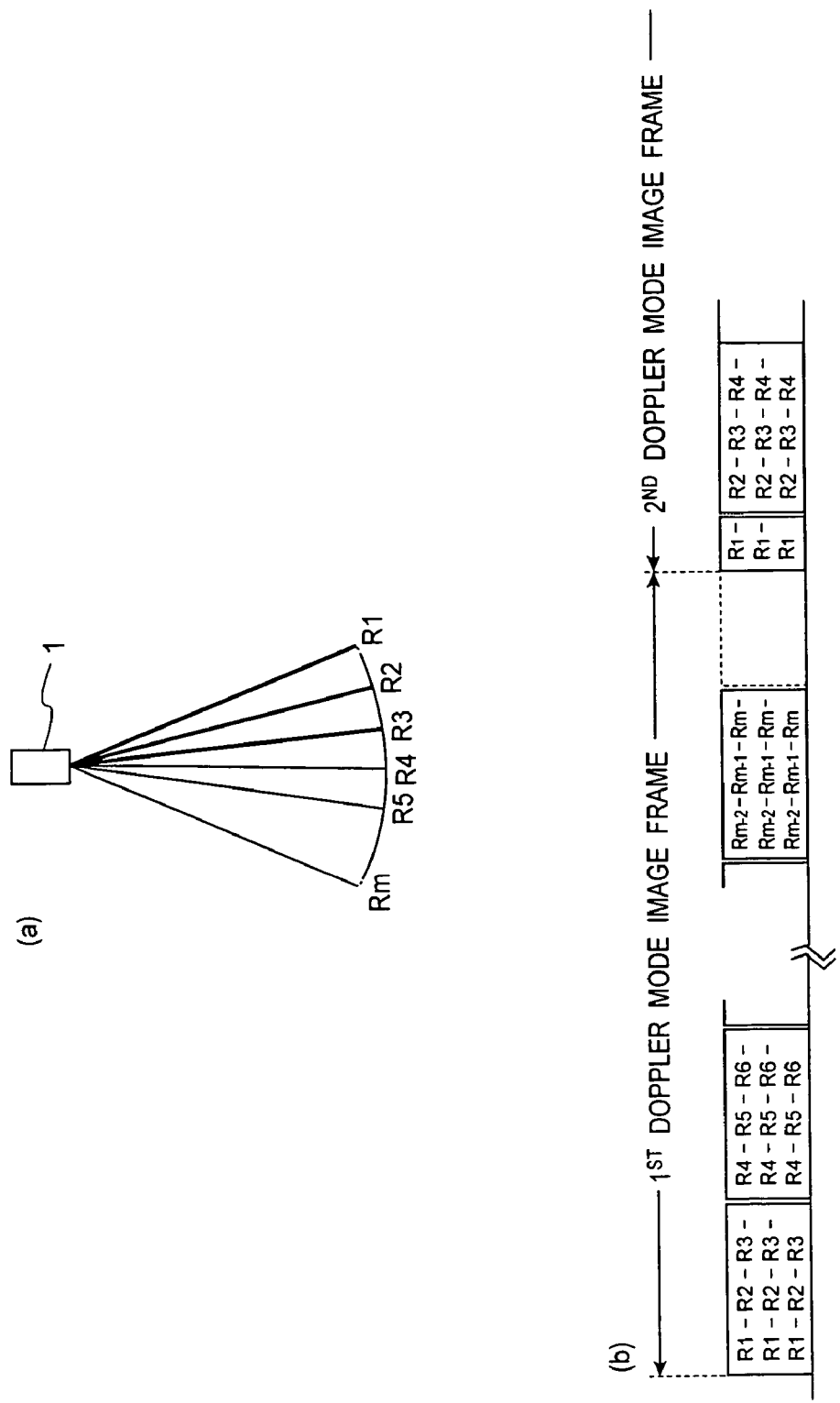
FIG. 12 is an illustration showing an example of a time chart for illustrating a modification to the second embodiment of the present invention.

FIG. 11 is an illustration showing an example of a time chart for illustrating a modification to the first embodiment. FIG. 12 is an illustration showing an example of a time chart for illustrating a modification to the second embodiment.

As shown in FIGS. 11 and 12, the first acquisition and storage in the raster direction R4 included in the second group of the first Doppler-mode image frame may be conducted immediately after the third acquisition and storage in the raster direction R3 included in the first group of the first Doppler-mode image frame. Except that there is no acquisition and storage of B-mode signals in between one group and the next of the Doppler-mode image frame, controls of the acquisition and storage may be similar to the first or second embodiment.

In FIG. 11, the last group of the first Doppler-mode image frame including the raster directions Rm-1 and Rm is combined with the first group of the second Doppler-mode image frame including the raster direction R1. As described in FIGS. 5 and 6, the acquisition and storage are controlled in the raster directions Rm-1, Rm, and R1 as one group. In FIG. 12, each acquisition and storage in the raster direction R1 included in the first group of the second Doppler-mode image frame is conducted after the first break period as described in FIGS. 8 and 9. The first break period can be replaced with the dummy acquisition and storage as described in FIG. 10.

Since the acquisition and storage are conducted n times (e.g., n=3) for each of Q raster directions (e.g., Q=3) included in one group of the Doppler-mode image frame, a time difference occurs between one group and the next of the Doppler-mode image frame. This may result in appearance of boundary discontinuity at positions between one group and the next. However, by applying the controls described in the first or second embodiment, such discontinuity may become indistinctive when a plurality of Doppler-mode image frames are displayed in the monitor 33.

In the first and second embodiments, the acquisition and storage have been described to be conducted for one group of a B-mode image frame and after one group of an Doppler-mode image frame. However, the acquisition and storage in a plurality of groups of the B-mode image frame may alternatively be conducted after those in a plurality of groups of the Doppler-mode image frame.

Although the autocorrelation unit has been described for detecting Doppler-mode signals, a FFT (Fast Fourier Transformation) unit may alternatively be used for the detection. Doppler-mode signals detected by the Doppler-mode processing unit 5 may include information of tissue motion, such as, for example, the myocardium, instead of or in addition to the blood flow.

Instead of displaying the acquired image frames in the monitor 33, the acquired image frames may be transmitted as image data to a display apparatus provided independently of the ultrasound diagnosis apparatus. Further, the acquired image frames may alternatively be stored as image data in a detachable memory medium which may be used in a display apparatus provided independently of the ultrasound diagnosis apparatus. The acquired image frames maybe displayed in the display apparatus.

The embodiments described above are examples described only for making it easier to understand the present invention, and are not described for the limitation of the present invention. Consequently, each component and element disclosed in the embodiments of the present invention may be redesigned or modified to its equivalent within a scope of the present invention Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An ultrasound diagnosis apparatus, comprising:
a probe configured to perform an alternating scan along a raster in each of plural Doppler groups of ultrasound beam directions so as to acquire first and second Doppler-mode image frames;
a controller coupled to the probe and configured to control the probe to treat a last group of the ultrasound beam directions for the first Doppler-mode image frame and an initial group of the ultrasound beam directions for the second Doppler-mode image frame as one Doppler group of the ultrasound beam directions;
a processor coupled to the probe and configured to detect a Doppler-mode signal based on the alternating scan along a raster so as to prepare the first and second Doppler-mode image frames; and an output unit coupled to the processor and configured to output the prepared first and second Doppler-mode image frames.

2. The apparatus according to claim 1, wherein the second Doppler-mode image frame is acquired next to the first Doppler-mode image frame.

3. The apparatus according to claim 1, wherein the output unit is a display unit configured to display the first and second Doppler-mode image frames.

4. The apparatus according to claim 1, wherein the output unit transmits the first and second Doppler-mode image frames through network.

5. The apparatus according to claim 1, wherein the output unit stores the first and second Doppler-mode image frames in a memory medium.

6. The apparatus according to claim 1, wherein the processor is further configured to prepare a processed Doppler-mode image frame based on at least the first and second Doppler-mode image frames, and the output unit outputs the processed Doppler-mode image frame as the prepared first Doppler-mode image frame.

7. The apparatus according to claim 6, wherein the processor prepares the processed Doppler-mode image frame by averaging at least the first and second Doppler-mode image frames.

8. The apparatus according to claim 6, wherein the processor prepares the processed Doppler-mode image frame by weighting at least the first and second Doppler-mode image frames.

9. The apparatus according to claim 1, wherein the processor is further configured to perform a B-mode scan in an interval between the alternating scan along a raster in a first Doppler group of the ultrasound beam directions and the alternating scan along a raster in a second Doppler group of the ultrasound beam directions.

10. The apparatus according to claim 1, wherein the probe is further configured to perform B-mode groups of B-mode scan with at least one ultrasound beam so as to acquire first and second B-mode image frames, the B-mode groups being performed in at least two intervals between the Doppler groups for each of the first and second B-mode image frames; the processor is further configured to detect a B-mode signal based on the B-mode scan so as to prepare the first and second B-mode image frames; the controller is further configured to control the probe so that a first boundary position in the first B-mode image frame originating from one and a next B-mode groups of the B-mode scan differs from a second boundary position in the second B-mode image frame originating from one and a next B-mode groups of the B-mode scan; and the output unit is further configured to output the prepared first and second B-mode image frames.

11. The apparatus according to claim 10, wherein the second B-mode image frame is acquired next to the first B-mode image frame.

12. The apparatus according to claim 10, wherein the controller treats a last group of the B-mode scan for the first B-mode image frame and an initial group of the B-mode scan for the second B-mode image frame as one B-mode group of the B-mode scan.

13. The apparatus according to claim 10, wherein a number of the ultrasound beams in an initial B-mode group of the B-mode scan for the second B-mode image frame is fewer than a number of the ultrasound beams in a next B-mode group of the B-mode scan for the second B-mode image frame.

14. The apparatus according to claim 13, wherein the probe stops scanning for a period corresponding to a difference between the numbers of the ultrasound beams in the initial B-mode group and the next B-mode group after the B-mode scan for the first B-mode image frame.

15. The apparatus according to claim 13, wherein the probe scans in a field other than the second B-mode image frame for a period corresponding to a difference between the numbers of the ultrasound beams in the initial B-mode group and the next B-mode group after the B-mode scan for the first B-mode image frame.

16. The apparatus according to claim 10, wherein the processor is further configured to prepare a processed B-mode image frame based on at least the first and second B-mode image frames, and the output unit outputs the processed B-mode image frame as the prepared first B-mode image frame.

17. The apparatus according to claim 16, wherein the processor prepares the processed B-mode image frame by averaging at least the first and second B-mode image frames.

18. The apparatus according to claim 16, wherein the processor prepares the processed B-mode image frame by weighting at least the first and second B-mode image frames.

19. An ultrasound diagnosis apparatus for obtaining first and second Doppler-mode image frames, the apparatus comprising:

a probe configured to perform an interleaving scan for each of the first and second Doppler-mode image frames, each of the first and second Doppler-mode image frames being divided into a plurality of interleaving scan groups;

a controller configured to control the probe so that a last group of the interleaving scan groups in the first Doppler-mode image frame has a smaller size than another one of the interleaving scan groups in the first Doppler-mode image frame; an initial group of the interleaving scan groups in the second Doppler-mode image frame has a smaller size than another one of the interleaving scan groups in the second Doppler-mode image frame; and a combined size of the last and initial interleaving scan groups is similar to a size of the another one of the interleaving scan groups in one of the first and second Doppler-mode image frames;

a processor coupled to the probe and configured to detect a Doppler-mode signal based on the interleaving scan so as to prepare the first and second Doppler-mode image frames; and an output unit coupled to the processor and configured to output the prepared first and second Doppler-mode image frames.

20. An ultrasound diagnosis apparatus, comprising:

a probe configured to perform an interleaving scan in Doppler groups of ultrasound beam directions so as to acquire first and second Doppler-mode image frames;

a controller coupled to the probe and configured to control the probe to perform the interleaving scan for an initial group of the second Doppler-mode image frame after the interleaving scan for a last group of the first Doppler-mode image frame, wherein the initial group includes fewer ultrasound beam directions than a next group of the ultrasound beam directions for the second Doppler-mode image frame;

a processor coupled to the probe and configured to detect a Doppler-mode signal based on the interleaving scan so as to prepare the first and second Doppler-mode image frames; and an output unit coupled to the processor and configured to output the prepared first and second Doppler-mode image frames.

21. The apparatus according to claim 20, wherein the probe stops scanning for a period corresponding to a difference between the numbers of the ultrasound beams in the initial group and the next group after the interleaving scan for the last group of the first Doppler-mode image frame.

22. The apparatus according to claim 20, wherein the probe scans in a field other than the second Doppler-mode image frame for a period corresponding to a difference between the numbers of the ultrasound beams in the initial group and the next group after the interleaving scan for the last group of the first Doppler-mode image frame.

23. The apparatus according to claim 20, wherein the second Doppler-mode image frame is acquired next to the first Doppler-mode image frame.

24. The apparatus according to claim 20, wherein the output unit is a display unit configured to display the first and second Doppler-mode image frames.

25. The apparatus according to claim 20, wherein the output unit transmits the first and second Doppler-mode image frames through network.

26. The apparatus according to claim 20, wherein the output unit stores the first and second Doppler-mode image frames in a memory medium.

27. The apparatus according to claim 20, wherein the processor is further configured to prepare a processed Doppler-mode image frame based on at least the first and second Doppler-mode image frames, and the output unit outputs the processed Doppler-mode image frame as the prepared first Doppler-mode image frame.

28. The apparatus according to claim 27, wherein the processor prepares the processed Doppler-mode image frame by averaging at least the first and second Doppler-mode image frames.

29. The apparatus according to claim 27, wherein the processor prepares the processed Doppler-mode image frame by weighting at least the first and second Doppler-mode image frames.

30. The apparatus according to claim 20, wherein the processor is further configured to perform a B-mode scan in an interval between the interleaving scan in a first Doppler group of the ultrasound beam directions and the interleaving scan in a second Doppler group of the ultrasound beam directions.

31. The apparatus according to claim 20, wherein the probe is further configured to perform B-mode groups of B-mode scan with at least one ultrasound beam so as to acquire first and second B-mode image frames, the B-mode groups being performed in at least two intervals between the Doppler groups for each of the first and second B-mode image frames; the processor is further configured to detect a B-mode signal based on the B-mode scan so as to prepare the first and second B-mode image frames; the controller is further configured to control the probe so that a first boundary position in the first B-mode image frame originating from one and a next B-mode groups of the B-mode scan differs from a second boundary position in the second B-mode image frame originating from one and a next B-mode groups of the B-mode scan; and the output unit is further configured to output the prepared first and second B-mode image frames.

32. The apparatus according to claim 31, wherein the second B-mode image frame is acquired next to the first B-mode image frame.

33. The apparatus according to claim 32, wherein the controller treats a last group of the B-mode scan for the first B-mode image frame and an initial group of the B-mode scan for the second B-mode image frame as one B-mode group of the B-mode scan.

34. The apparatus according to claim 31, wherein a number of the ultrasound beams in an initial group of the B-mode scan for the second B-mode image frame is fewer than a number of the ultrasound beams in a next group of the B-mode scan for the second B-mode image frame.

35. The apparatus according to claim 34, wherein the probe stops scanning for a period corresponding to a difference between the numbers of the ultrasound beams in the initial group of the B-mode scan and the next group of the B-mode scan after the B-mode scan for the first B-mode image frame.

36. The apparatus according to claim 34, wherein the probe scans in a field other than the second B-mode image frame for a period corresponding to a difference between the numbers of the ultrasound beams in the initial group of the B-mode scan and the next group of the B-mode scan after the B-mode scan for the first B-mode image frame.

37. The apparatus according to claim 31, wherein the processor is further configured to prepare a processed B-mode image frame based on at least the first and second B-mode image frames, and the output unit outputs the processed B-mode image frame as the prepared first B-mode image frame.

38. The apparatus according to claim 37, wherein the processor prepares the processed B-mode image frame by averaging at least the first and second B-mode image frames.

39. The apparatus according to claim 37, wherein the processor prepares the processed B-mode image frame by weighting at least the first and second B-mode image frames.

40. An ultrasound diagnosis apparatus, comprising:
a probe configured to perform an alternating scan along a raster in each of plural groups of ultrasound beam directions so as to acquire first and second Doppler-mode image frames;
a controller coupled to the probe and configured to control the probe to perform the alternating scan along a raster for a last group of the ultrasound beam directions for the first Doppler-mode image frame before the alternating scan along a raster for an initial group of the ultrasound beam directions for the second Doppler-mode image frame, wherein the last group includes fewer ultrasound beam directions than a previous group of the ultrasound beam directions for the first Doppler-mode image frame;
a processor coupled to the probe and configured to detect a Doppler-mode signal based on the alternating scan along a raster so as to prepare the first and second Doppler-mode image frames; and
an output unit coupled to the processor and configured to output the prepared first and second Doppler-mode image frames.

41. The apparatus according to claim 40, wherein the probe stops scanning for a period corresponding to a difference between the numbers of the ultrasound beams in the last group and the previous group before the alternating scan along a raster for the initial group.

42. The apparatus according to claim 40, wherein the probe scans in a field other than the first Doppler-mode image frame for a period corresponding to a difference between the numbers of the ultrasound beams in the last group and the previous group before the alternating scan along a raster for the initial group.

43. An ultrasound diagnosis apparatus for obtaining first and second Doppler-mode image frames, the apparatus comprising:

an ultrasound generator configured to generate a plurality of ultrasound beams in different directions for each of the first and second Doppler-mode image frames;

a controller coupled to the ultrasound generator and configured to divide the plurality of ultrasound beams into groups, each of a second group to one before a last group of the groups including a first predetermined number N (N≧2) of the ultrasound beams, the last group for the first Doppler-mode image frame including a second predetermined number M (1≦M≦N−1) of the ultrasound beams, an initial group of the groups for the second Doppler-mode image frame including a third predetermined number N−M of the ultrasound beams, wherein the controller is further configured to control the ultrasound generator to repeat the N ultrasound beams more than once in every one of the second group to the one before the last group and in the last and initial groups as one group;

a processor coupled to the ultrasound generator and configured to detect a Doppler-mode signal based on echo signals resulting from the ultrasound beams and to prepare the first and second Doppler-mode image frames based on the detected Doppler-mode signal; and an output unit coupled to the processor and configured to output the prepared first and second Doppler-mode image frames.

44. A method of ultrasound scanning, comprising:

alternating scanning along a raster in groups of ultrasound beam directions so as to acquire first and second Doppler-mode image frames;

controlling the alternating scanning along a raster to treat a last group of the ultrasound beam directions for the first Doppler-mode image frame and an initial group of the ultrasound beam directions for the second Doppler-mode image frame as one group of the ultrasound beam directions;

detecting a Doppler-mode signal based on the alternating scanning along a raster;

preparing the first and second Doppler-mode image frames based on the detected Doppler-mode signal; and outputting the prepared first and second Doppler-mode image frames.

\* \* \* \* \*

UNITED STATES PATENT AND TRADEMARK OFFICE
CERTIFICATE OF CORRECTION

| | | |
|---|---|---|
| PATENT NO. | : 7,371,219 B2 | Page 1 of 1 |
| APPLICATION NO. | : 10/839128 | |
| DATED | : May 13, 2008 | |
| INVENTOR(S) | : Sakaguchi et al. | |

It is certified that error appears in the above-identified patent and that said Letters Patent is hereby corrected as shown below:

On the title page, Item (30), the Foreign Application Priority Data is missing. Item (30) should read:

-- (30)            Foreign Application Priority Data

May 8, 2003      (JP)      -------------------------- 2003-130330 --

Signed and Sealed this

Twenty-ninth Day of July, 2008

JON W. DUDAS
*Director of the United States Patent and Trademark Office*